(12) United States Patent
Gomurashvili et al.

(10) Patent No.: US 11,680,141 B2
(45) Date of Patent: Jun. 20, 2023

(54) HYDROGEL MATERIALS FOR OBTURATION

(71) Applicant: SONENDO, INC., Laguna Hills, CA (US)

(72) Inventors: Zaza Gomurashvili, Tustin, CA (US); Carlos Enrique Zamora Salgado, Buena Park, CA (US); David Tobia, Laguna Hills, CA (US); Mehrzad Khakpour, Laguna Hills, CA (US); Bjarne Bergheim, Laguna Hills, CA (US)

(73) Assignee: Sonendo, Inc., Laguna Hills, CA (US)

( * ) Notice: Subject to any disclaimer, the term of this patent is extended or adjusted under 35 U.S.C. 154(b) by 442 days.

(21) Appl. No.: 16/865,208

(22) Filed: May 1, 2020

(65) Prior Publication Data
US 2020/0347191 A1 Nov. 5, 2020

Related U.S. Application Data

(60) Provisional application No. 62/971,620, filed on Feb. 7, 2020, provisional application No. 62/842,387, filed on May 2, 2019.

(51) Int. Cl.
| | | |
|---|---|---|
| *C08J 3/075* | (2006.01) | |
| *A61K 6/887* | (2020.01) | |
| *A61K 6/54* | (2020.01) | |
| *A61C 5/70* | (2017.01) | |
| *C08F 20/06* | (2006.01) | |
| *C08F 20/56* | (2006.01) | |
| *C08K 5/18* | (2006.01) | |
| *C08K 3/30* | (2006.01) | |

(52) U.S. Cl.
CPC .............. *C08J 3/075* (2013.01); *A61K 6/54* (2020.01); *A61K 6/887* (2020.01); *A61C 5/70* (2017.02); *C08F 20/06* (2013.01); *C08F 20/56* (2013.01); *C08J 2333/08* (2013.01); *C08J 2333/26* (2013.01); *C08K 5/18* (2013.01); *C08K 2003/3045* (2013.01)

(58) Field of Classification Search
CPC ...................................................... A61K 6/54
See application file for complete search history.

(56) References Cited

U.S. PATENT DOCUMENTS

| | | | | |
|---|---|---|---|---|
| 8,062,673 B2 * | 11/2011 | Figuly | ................ | A61K 9/0024 |
| | | | | 424/1.29 |
| 2003/0211083 A1 * | 11/2003 | Vogel | ................ | A61L 27/3834 |
| | | | | 435/366 |

FOREIGN PATENT DOCUMENTS

| | | |
|---|---|---|
| CA | 2031739 A1 * 6/1991 | |
| EP | 0685454 A1 * 12/1995 | |
| WO | WO-2004032881 A2 * 4/2004 | ........... A61K 9/5031 |

OTHER PUBLICATIONS

English machine translation of Rheinberger et al. (EP 0 685 454) (Year: 1995).*
2-propanol SDS; Sigma-Aldrich.*

* cited by examiner

*Primary Examiner* — Michael F Pepitone
(74) *Attorney, Agent, or Firm* — Knobbe, Martens, Olson & Bear, LLP

(57) ABSTRACT

A curable mixture and method of using the mixture are disclosed. In some embodiments, the mixture comprises a water soluble acrylate-based monomer, a water-soluble acrylamide-based monomer, or a mixture thereof, and has properties suitable for use as a tooth filling after curing.

25 Claims, 5 Drawing Sheets

HYDROGEL MATERIALS FOR OBTURATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority to U.S. Provisional Patent Application No. 62/842,387 filed May 2, 2019, and to U.S. Provisional Patent Application 62/971,620 filed Feb. 7, 2020, the contents of each of which are incorporated by reference herein in their entirety for all purposes.

BACKGROUND

In conventional endodontic procedures, an opening is drilled through the crown of a diseased tooth, and endodontic files are inserted into the root canal system to open the canal spaces and remove organic material therein. The root canal is then filled with solid matter such as gutta percha and an obturation material, and the tooth is restored. However, this procedure may not remove all organic material from the canal spaces, which can lead to post-procedure complications such as infection. In addition, motion of the endodontic file may force organic material through an apical opening into periapical tissues. In some cases, the end of the endodontic file itself may pass through the apical opening. Such events may result in trauma to the soft tissue near the apical opening and lead to post-procedure complications.

Current treatment techniques for tooth decay (caries) generally include mechanical removal of the caries and diseased tissue (e.g., using dental burs, excavators, etc.), which will expose healthy dentin. However, the bur (or other mechanical instrument) may not differentiate between diseased and healthy dentin, and other instruments such as excavators and explorers may not be able to accurately determine the extent to which tooth removal should continue. This may result in either incomplete removal of caries or overly-aggressive removal of healthy dentin, which may in turn reduce the longevity of the tooth. The removed portions of the tooth can then be filled with solid matter such as composite, gold, porcelain, etc., and the tooth can be restored. However, this procedure may not remove all decayed material from the tooth, which combined with inadequate penetration of the restorative material can result in bacterial leakage and subsequently post-procedure complications such as infection or recurrent caries. In part to minimize the risk of reinfection, endodontic material placement typically requires the use of a gutta percha point to encourage penetration of the obturation material into lateral canals and isthmi. In addition, the use of a dental drill and anesthetics may be uncomfortable for the patient. Various filling spaces within or adjacent to a tooth can benefit from improvements in dental treatment techniques. Examples of such filling spaces include but are not limited to root canals, cavities resulting from the removal of caries, other openings such as cracks and gaps, and/or missing portions of teeth (e.g., resulting from fracture and/or wear). Accordingly, it can be advantageous to provide improved compositions, methods and apparatus for treating dental decay.

More recently, dental apparatuses have been developed that can deliver a curable mixture to a treatment region without the necessity of an obturation point. (See U.S. Pat. No. 9,877,801, the entire contents of which are hereby incorporated herein by reference for all purposes). Various formulations are known that can be used as curable mixtures. However, the compatibility of current materials with the new technology is less than desired. Thus, the need for more advanced obturation materials is needed.

SUMMARY

Various non-limiting aspects of the present disclosure are provided to illustrate features of the disclosed compositions, apparatus and methods. Examples of compositions comprising curable materials for filling a tooth space are provided. A method of using the compositions for endodontic treatment, or for filling a dental treatment region comprising a tooth space such as a cavity, root canal, or crack, is provided. A method of using a dental apparatus to deliver the curable material to a tooth region is also provided. The dental apparatus may comprise a pressure wave generator to generate pressure waves to deliver the curable material throughout the tooth space. Further, a method for supplying a two-part curable composition to a dental apparatus to fill a tooth space with a curable mixture is provided.

In one aspect, a curable mixture of ingredients is provided. The curable mixture includes (a) a water soluble acrylate-based monomer, a water-soluble acrylamide-based monomer, a water-soluble chelating monomer, or a mixture thereof; (b) a free-radical polymerization initiator; (c) a radiopaque material; and (d) an aqueous carrier having a pH in the range of about 7.0 to about 8.4.

In various embodiments the ingredients (a), (b), (c), and (d) are selected to provide the curable mixture with properties suitable for use as a tooth filling after curing of the curable mixture to form a cured mixture by a polymerization of ingredient (a) that is initiated by ingredient (b).

In another aspect, a curable mixture of ingredients is provided. The curable mixture includes (a) a water-soluble acrylate-based monomer, a water-soluble acrylamide-based monomer, a water-soluble chelating monomer, or a mixture thereof; (b) a free-radical polymerization initiator; (c) a radiopaque material; and (d) an aqueous carrier having a pH in the range of about 7.0 to about 8.4; wherein the ingredients (a), (b), (c), and (d) are selected to provide the curable mixture with properties suitable for use as a tooth filling after curing of the curable mixture to form a cured mixture by a polymerization of ingredient (a) that is initiated by ingredient (b).

In some embodiments, the free radical initiator comprises a light initiator, thermal initiator, or both light initiator and a thermal initiator. In some embodiments, the water-soluble acrylamide-based monomer comprises 3-acrylamidopropyl trimethylammonium chloride, 3-methacrylamidopropyl trimethylammonium chloride, 3-acrylamidopropyl trimethylammonium methyl sulfate, 3-methacrylamidopropyl trimethylammonium methyl sulfate, or a combination thereof. In some embodiments, the water-soluble acrylate-based monomer comprises [2-(methacryloyloxy)ethyl] trimethylammonium chloride, [2-(acryloyloxy)ethyl] trimethylammonium chloride, [2-(acryloyloxy)ethyl] trimethylammonium methyl sulfate, [2-(methacryloyloxy)ethyl] trimethylammonium methyl sulfate, (hydroxyethyl)methacrylate (HEMA), or a combination thereof. In some embodiments, the water-soluble acrylate-based monomer comprises poly(ethylene glycol) diacrylate, ethoxylated trimethylolpropane triacrylate, or a combination thereof.

In some embodiments, the chelating monomer comprises 4-methacryloxyethyl trimellitic acid (4-MET) or glycerol phosphate dimethacrylate (GPDM). In some embodiments, the radiopaque material comprises a polymerizable radiopaque monomer or radiopaque salt. In some embodiments, the radiopaque material comprises sodium diatrizoate hydrate or iodophenyl functionalized polyethylene glycol. In some embodiments, the radiopaque material comprises a water soluble radiopaque aromatic acid derived (meth)acrylate. In some embodiments, the curable mixture comprises 5-acrylamido-2,4,6 triiodo isophthalic acid.

In some embodiments, the curable mixture is provided in two parts, each of which comprises a liquid. In some embodiments, each of the two liquid part is degassed. In some embodiments, the curable mixture further comprises a polymerization cross-linker. In some embodiments, the polymerization cross-linker comprises N,N'-methylenebis (acrylamide) (MBAA), triethylene glycol dimethacrylate (TEGDMA), or a combination thereof.

In some embodiments, the free radical initiator comprises a light initiator. In some embodiments, the curable mixture of ingredients comprises camphorquinone (CQ), 7,7-dimethyl-2,3-dioxobicyclo[2.2.1] heptane-1-carboxylic acid (CCQ), 1-phenyl-1,2-propanedione (PPD), 2,2'-azobis[2-methyl-N-(2-hydroxyethyl)propionamide (VA-086). In some embodiments, the curable mixture of ingredients comprises a co-initiator selected from N-phenylglycine, 2-pyrrolidinone, dimethylaminoethyl acrylate (DMAEA), triethanolamine (TEOA), 1-vinyl-2-pyrrolidone and L-arginine. In some embodiments, the free radical initiator comprises a heat initiator. In some embodiments, the heat initiator comprises 2,2'-azobis[2-(2-imidazolin-2-yl) propane] dihydrochloride. In some embodiments, wherein the initiator comprises potassium persulfate, and further comprises triethanolamine.

In some embodiments, the curable mixture further comprises methacrylic acid. In some embodiments, the curable mixture comprises from 20 wt % to 60 wt % of the aqueous carrier, based on the weight of the curable mixture.

In another aspect, an obturation material for use as a radiopaque tooth filling after curing is provided. The obturation material is provided as two or more liquid parts, including (a) a water-soluble acrylate-based monomer, a water-soluble acrylamide-based monomer, a water-soluble chelating monomer, or a mixture thereof; (b) a free-radical polymerization initiator; (c) a water soluble radiopaque material; and (d) an aqueous carrier; wherein at least one liquid part has a viscosity less than 60 cP (at 25° C.), wherein (a), (b), (c), and (d) are selected to form a curable mixture, and wherein the obturation material is curable in a tooth by a polymerization of ingredient (a) that is initiated by ingredient (b).

In some embodiments, at least one liquid part has a viscosity less than 20 cP (25° C.) and at least one liquid part has a viscosity less than 60 cP (° 25 C.) for a time sufficient to fill a root canal of a tooth. In some embodiments, each of the two or more liquid parts is a degassed liquid. In some embodiments, each of the two or more degassed liquid parts has a percent oxygen content reduction of at least 10%. In some embodiments, the free radical initiator comprises a light initiator or a thermal initiator. In some embodiments, the free radical initiator comprises a light initiator and a thermal initiator. In some embodiments, the obturation material is heat curable upon exposure to human body temperature, and the obturation material has a Shore A hardness of at least 40 when cured.

In some embodiments, the water-soluble acrylate-based monomer comprises [2-(methacryloyloxy)ethyl] trimethyl-ammonium chloride, [2-(acryloyloxy)ethyl] trimethylammonium chloride, [2-(acryloyloxy)ethyl] trimethylammonium methyl sulfate, [2-(methacryloyloxy)ethyl] trimethylammonium methyl sulfate, (hydroxyethyl)methacrylate (HEMA), or a combination thereof. In some embodiments, the water-soluble acrylate-based monomer comprises poly(ethylene glycol) diacrylate, ethoxylated trimethylolpropane triacrylate, or a combination thereof. In some embodiments, the radiopaque material comprises sodium diatrizoate hydrate, iodophenyl functionalized polyethylene glycol comprising 5-acrylamido-2,4,6 triiodo isophthalic acid. In some embodiments, obturation material comprises a cross-linker comprises N,N'-methylenebis(acrylamide) (MBAA), triethylene glycol dimethacrylate (TEGDMA), or a combination thereof. In some embodiments, the obturation material has a hardness value of at least 40 Shore A within 40 seconds of exposure to light energy.

In another aspect, a curable mixture of ingredients is provided. The curable mixture includes (a) 20 wt. % to 50 wt % poly(ethylene glycol) diacrylate (PEG); (b) 0.5 wt % to 1.5 wt. % N,N'-methylenebis(acrylamide) (MBAA); (c) 0.2 wt. % to 1.5 wt % potassium persulfate; (d) 0.2 wt. % to 0.6 wt % triethanolamine; (e) 5 wt % to 30 wt. % of 5-acrylamido-2,4,6-triiodo isophthalic acid; and (f) 20 wt % to 60 wt % of an aqueous carrier, wherein the ingredients are selected to provide the curable mixture with properties suitable for use as a tooth filling after curing of the curable mixture to form a cured mixture.

In some embodiments, the curable mixture further comprises 0.5 wt. % to 2.5 wt % of [2-(acryloyloxy)ethyl] trimethyl-ammonium chloride (EGAA-QCl). In some embodiments, the curable mixture further comprises 20 wt % to 50 wt % ethoxylated trimethylolpropane triacrylate. In some embodiments, a cured hydrogel polymer is formed from the curable mixture, having a Shore A hardness value of at least 70, is provided.

In another aspect, a curable mixture of ingredients is provided. The curable mixture includes (a) 0.1 wt % to 0.5 wt % 2,2'-azobis[2-(2-imidazolin-2-yl) propane] dihydrochloride; (b) 20 wt % to 50 wt % ethoxylated trimethylolpropane triacrylate; (c) 10 wt % to 15 wt % poly(ethylene glycol) diacrylate (PEG); (d) 5 wt % to 35 wt % 5-acrylamido-2,4,6-triiodo isophthalic acid and (f) 15 wt % to 50 wt % water.

In some embodiments, the curable mixture is provided in two parts, and wherein the ingredients are selected to provide the curable mixture with properties suitable for use as a tooth filling after curing of the curable mixture to form a cured mixture. In some embodiments, the two parts are degassed liquids. In some embodiments, curable mixture further comprises 0.5 wt. % to 2.5 wt % of [2-(acryloyloxy) ethyl] trimethyl-ammonium chloride (EGAA-QCl). In some embodiments, a cured hydropolymer prepared from the curable mixture, and having a Shore A hardness value of at least 70, is provided.

In another aspect, a curable mixture of ingredients is provided. The curable mixture includes (a) 0.1 wt % to 0.5 wt % 2,2'-azobis[2-(2-imidazolin-2-yl) propane] dihydrochloride; (b) 0.1 wt % to 2.5 wt % of a light cure initiator; (c) 10 wt % to 30 wt % poly(ethylene glycol) diacrylate; (d) 0.5 wt % to 2 wt % N,N'-methylenebis (acrylamide) (MBAA); (e) optionally, 0.1 wt % to 1 wt % [2-(acryloyloxy)ethyl] trimethyl-ammonium chloride; and (f) an aqueous carrier, wherein the ingredients are selected to provide the curable mixture with properties suitable for use as a tooth filling after curing of the curable mixture to form a cured mixture.

In some embodiments, the light cure initiator comprises camphorquinone (CQ), 7,7-dimethyl-2,3-dioxobicyclo [2.2.1] heptane-1-carboxylic acid (CCQ), 1-phenyl-1,2-propanedione (PPD), 2,2'-azobis[2-methyl-N-(2-hydroxyethyl) propionamide, or a mixture thereof. In some embodiments, the light cure initiator comprises 2,2'-azobis[2-methyl-N-(2-hydroxyethyl)propionamide. In some embodiments, the curable mixture comprises a co-initiator selected from N-phenylglycine, 2-pyrrolidinone, dimethylaminoethyl acrylate (DMAEA), triethanolamine (TEOA), 1-vinyl-2-pyrrolidone and L-arginine, or a mixture thereof. In some embodiments, the curable mixture comprises 10 wt % to 40 wt % diatrizoate sodium hydrate.

In another aspect, a curable mixture of ingredients is provided. The curable mixture includes (a) 20 wt % to 50 wt % ethoxylated trimethylolpropane triacrylate; (b) 10 wt % to 15 wt % poly(ethylene glycol) diacrylate; (c) 0.1 wt % to 3 wt % 2,2'-azobis[2-methyl-N-(2-hydroxyethyl)propionamide; (d) 5-acrylamido-2,4,6-triiodo isophthalic acid; and (e) 15 wt % to 55 wt % aqueous carrier; wherein the ingredients are selected to provide the curable mixture with properties suitable for use as a tooth filling after curing of the curable mixture to form a cured mixture.

In some embodiments, the curable mixture has a Shore A hardness value greater than 50 when cured. In some embodiments, the curable mixture further comprises a co-initiator selected from a co-initiator selected from N-phenylglycine, 2-pyrrolidinone, dimethylaminoethyl acrylate (DMAEA), triethanolamine (TEOA), 1-vinyl-2-pyrrolidone and L-arginine.

In another aspect, a method of preparing a hydrogel comprising forming a reaction mixture comprising the curable mixture or obturation material is provided. The reaction mixture forms the hydrogel upon exposure to human body temperature for a period of time effective to cure the curable mixture. In some embodiments, the method further comprises degassing the reaction mixture prior to delivering the reaction mixture to a tooth inside the human body.

In another aspect, a method of filling a tooth is provided. The method includes identifying a tooth having a cavity in need of filling; positioning the curable mixture or obturation material within the cavity; and curing the curable mixture or obturation material within the cavity.

In another aspect, a method of filling a root canal is provided. The method includes identifying a tooth having a root canal in need of filling; positioning the curable mixture or obturation material within the root canal; and curing the curable mixture or obturation material within the root canal.

In another aspect, a method of filling a root canal with a hydrogel polymer is provided. The method includes (a) identifying a tooth having a root canal in need of filling; (b) positioning an aqueous curable mixture or obturation material within a handpiece, comprising delivering the curable mixture or obturation material to the handpiece in two liquid parts; (c) forming a liquid jet within the handpiece and using the liquid jet to deliver the two parts; (d) partially curing the curable mixture or obturation material within the root canal with light energy; and (e) exposing the partially cured mixture or obturation material within the root canal to heat to form a cured hydrogel polymer within the root canal.

Those skilled in the art will recognize that embodiments disclosed herein may achieve one advantage or group of advantages as taught herein without necessarily achieving other advantages as may be taught or suggested herein. Further, the foregoing is intended to summarize certain disclosed embodiments and is not intended to limit the scope of the embodiments, which may be disclosed in greater detail below.

BRIEF DESCRIPTION OF THE DRAWINGS

The foregoing and other features, aspects, and advantages of embodiments of the apparatus, compositions and methods of filling spaces in teeth are described in detail below with reference to the drawings, which are intended to illustrate and not to limit the embodiments. The drawings comprise the following FIGS. in which.

Figure 1A:
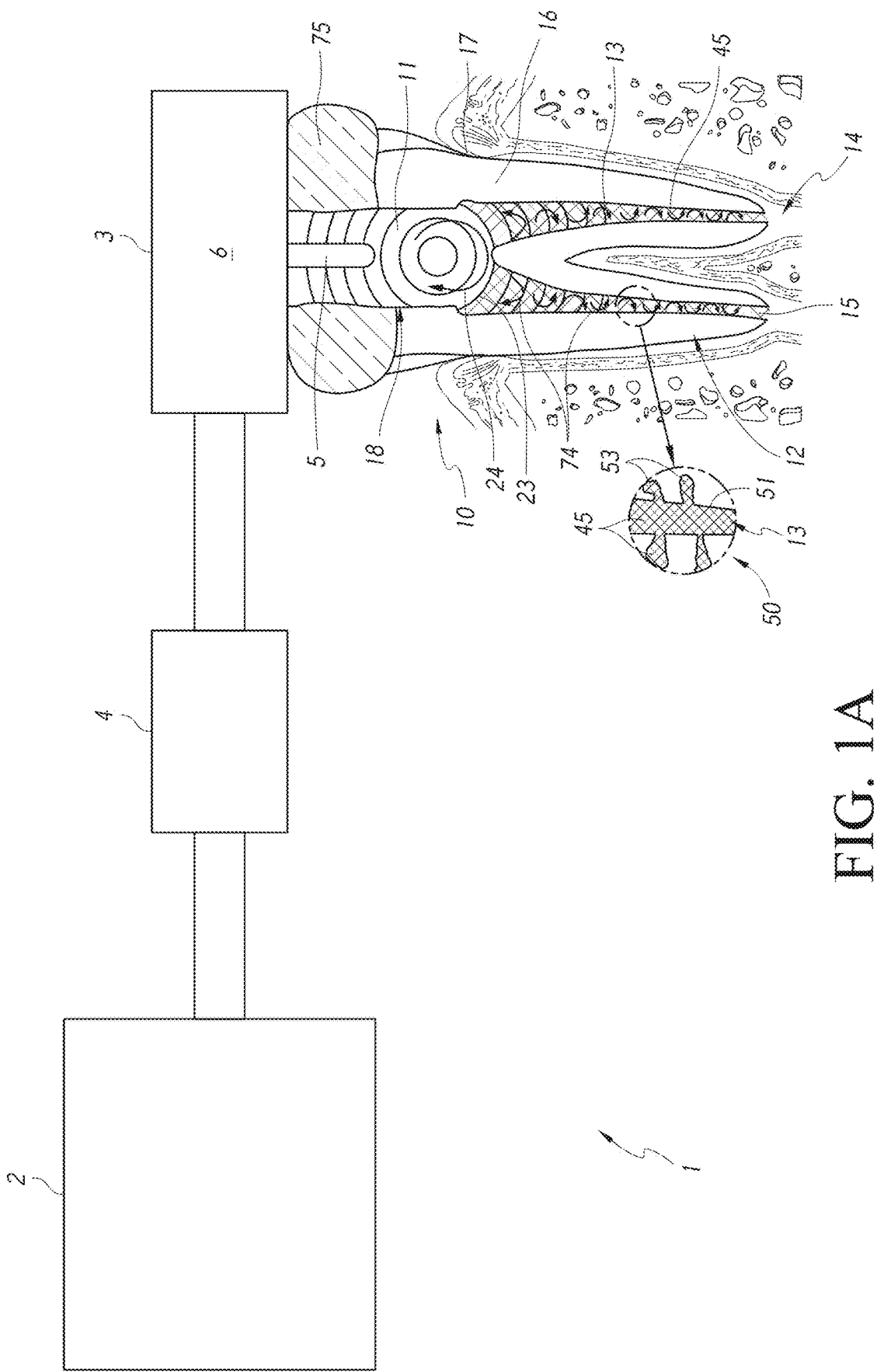
FIG. 1A is a schematic diagram of a dental treatment system for treating a root canal, according to various embodiments disclosed herein.

Throughout the drawings, reference numbers may be reused to indicate a general correspondence between referenced elements. The drawings are provided to illustrate examples of embodiments described herein and are not intended to limit the scope of the disclosure.

DETAILED DESCRIPTION

To protect the long-term health of the tooth, it can be advantageous to substantially fill the filling space or spaces of a tooth created from removal of caries, through root canal treatment, and/or natural wear. When the restoration follows a root canal treatment it can be important to fill not only the major canal spaces, but also any minor cracks and open spaces in the tooth with a filling material. Similarly, when the restoration follows a caries treatment it can be important to fill the resulting dental spaces in order to provide dimensional stability and/or structural integrity to the tooth.

In various embodiments, the filling material is an obturation material. The term "obturation material" refers to a material that is configured to fill root canals, restore carious lesions, and/or modify the surface of the tooth. The obturation material may be a polymerizable restorative composition that includes a curable mixture that is cured or hardened to form the final material, which may be referred to as a cured mixture or "tooth filling." It should be appreciated that terms such as setting, curing, hardening, cross-linking, polymerizing, and the like, refer to processes by which the obturation material components are transformed into a final hardened mixture in the tooth. In this context, an obturation material that is "suitable for use as a tooth filling" comprises a corresponding cured or hardened state having properties that meet standards set by an appropriate regulatory body (e.g., ISO 6876:2012—Dental root canal sealing materials). A cured obturation material having such properties is considered to meet the standards regardless of whether the regulatory body has provided official notification to that effect.

In some embodiments, various obturation material compositions or components thereof as described herein can be formed into a coherent collimated jet for delivery to a tooth space. For example, in an embodiment, an obturation material composition or components thereof, as described herein, can be formed into a liquid jet that forms a substantially parallel beam (e.g., is "collimated") over distances ranging from about 0.01 cm to about 10 cm. In some embodiments, the velocity profile transverse to the propagation axis of the jet is substantially constant (e.g., is "coherent"). For example, in some implementations, away from narrow boundary layers near the outer surface of the jet (if any), the jet velocity is substantially constant across the width of the jet. Therefore, in certain advantageous embodiments, the liquid jet (e.g., as delivered by an apparatus as described herein) may comprise a coherent, collimated jet (a "CC jet"). In some implementations, the CC jet may have velocities in a range from about 100 meters per second (m/s) to about 300 m/s, for example, about 190 m/s in some embodiments. In some implementations, the CC jet can have a diameter in a range from about 5 microns to about 1000 microns, in a range from about 10 microns to about 100 microns, in a range from about 100 microns to about 500 microns, or in a range from about 500 microns to about 1000 microns. Further details with respect to CC jets that can be comprised of obturation material compositions or components thereof as described herein can be found in U.S. Patent Publication No. 2007/0248932, which is hereby incorporated by reference herein in its entirety for all that it discloses or teaches.

In some embodiments, an obturation material comprises two or more components that react with one another to form a hardened obturation material. In other embodiments, the obturation or filling material may comprise a composition that is curable from a flowable state to a hardened state by exposure to an energy source such as light or heat, or both light and heat. In one embodiment, a curable mixture of ingredients comprises: (a) a water soluble acrylate-based monomer, a water-soluble acrylamide-based monomer, a water-soluble chelating monomer, or a mixture thereof; (b) free-radical polymerization initiator; (c) a radiopaque material; and (d) an aqueous carrier, wherein the ingredients (a), (b), (c), and (d) are selected to provide the curable mixture with properties suitable for use as a tooth filling after curing of the curable mixture to form a cured mixture by a polymerization of ingredient (a) that is initiated by ingredient (b). In one aspect, the cured obturation material may comprise a hydrogel material. The hydrogel material may comprise a hydrophilic polymer matrix or macromolecule that holds a large amount of water while maintaining structure as a hard gel, which is biocompatible and/or resistant to degradation in vivo.

Various water-soluble acrylate-based monomers and mixtures thereof are suitable for use in forming the curable mixture of ingredients. In some embodiments, the water-soluble acrylate-based monomer is a diacrylate monomer or a triacrylate monomer. In some embodiments, the water-soluble acrylate-based monomer is an acrylate monomer that is cationically charged, for example, an acrylate monomer that contains a quaternary ammonium group and a counterion. Examples include, but are not limited to, [2-(acryloyloxy)ethyl] trimethylammonium halide (e.g., halide is chloride counterion), [2-(methacryloyloxy)ethyl] trimethylammonium halide (e.g., halide is chloride counterion), [2-(acryloyloxy)ethyl] trimethylammonium methyl sulfate, and [2-(methacryloyloxy)ethyl] trimethylammonium methyl sulfate, and a combination of one or more thereof. In various embodiments, the cationically charged water-soluble acrylate-based monomer is present in an amount effective to inhibit bacterial growth in the resulting cured mixture. In some embodiments, the water-soluble acrylate-based monomer is an acrylate monomer that is uncharged. In some embodiments, the water-soluble acrylate-based monomer is polyethylene glycol diacrylate (PEG), ethoxylated trimethylolpropane triacrylate (ETT), (hydroxyethyl)methacrylate (HEMA), or a mixture thereof. In some embodiments, the water-soluble acrylate-based monomer is a high-molecular weight polyethylene glycol diacrylate (e.g., having a Mn of 700, or greater than 700). In some embodiments, the water soluble acrylate-based monomer, such as a triacrylate or diacrylate, may be present in an amount from 1 wt % to 75 wt %, 1 wt % to 60 wt %, 1 wt % to 50 wt %, 1 wt % to 25 wt %, 15 wt % to 75 wt %, 15 wt % to 60 wt %, 15 wt % to 58 wt %, 20 wt % to 60 wt %, 20 wt % to 58 wt %, 20 wt % to 50 wt %, 0.2 wt % to 10 wt %, or from or 0.2 wt % to 5 wt %, based on the total weight of the curable mixture. In some embodiments, the water soluble acrylate-based monomer, such as a triacrylate or diacrylate, may be present in an amount of, or of about, 0.1 wt %, 0.2 wt %, 0.5 wt %, 1 wt %, 5 wt %, 10 wt %, 15 wt %, 20 wt %, 25 wt %, 30 wt %, 40 wt %, 50 wt %, 58 wt %, 60 wt %, 75 wt %, 90 wt % or 100 wt. %, based on the total weight of the curable mixture, or any range of values therebetween.

Various water-soluble acrylamide-based monomers, and mixtures thereof, are suitable for use in the curable mixture of ingredients. In some embodiments, the water-soluble acrylamide-based monomer is an acrylamide monomer that is cationically charged, and for example, may contain a quaternary ammonium group and a counterion. Examples include, but are not limited to, 3-acrylamidopropyl trimethylammonium halide (e.g., halide is chloride counterion), 3-methacrylamidopropyl trimethylammonium halide (e.g., halide is chloride counterion), 3-acrylamidopropyl trimethylammonium methyl sulfate, and 3-methacrylamidopropyl trimethylammonium methyl sulfate, and a combination of one or more thereof. In some embodiments, a cationically charged water-soluble acrylamide-based monomer is present in an amount effective to inhibit bacterial growth in the resulting cured mixture. The water-soluble acrylamide-based monomer may comprise 3-acrylamidopropyl trimethylammonium chloride, 3-methacrylamidopropyl trimethylammonium chloride, 3-acrylamidopropyl trimethylammonium methyl sulfate, 3-methacrylamidopropyl trimethylammonium methyl sulfate, or a combination thereof. In some embodiments, a water soluble acrylamide-based monomer may be present in an amount from 1 wt % to 60 wt %, 1 wt % to 20 wt %, 1 wt % to 15 wt %, 20 wt % to 58 wt %, 20 wt % to 50 wt %, 0.2 wt % to 10 wt %, or from 0.2 wt % to 5 wt %, based on the total weight of the curable mixture. In some embodiments, the water soluble acrylamide-based monomer may be present in an amount of, or of about, 0.1 wt %, 0.2 wt %, 0.5 wt %, 1 wt %, 5 wt %, 10 wt %, 15 wt %, 20 wt %, 25 wt %, 30 wt %, 40 wt %, 50 wt %, 58 wt %, 60 wt %, 75 wt %, 90 wt % or 100 wt. %, based on the total weight of the curable mixture, or any range of values therebetween.

Various water-soluble chelating monomers and mixtures thereof are suitable for use in the curable mixture of ingredients. Examples of a chelating monomer include but are not limited to 4-methacryloxyethyl trimellitic acid (4-MET) and glycerol phosphate dimethacrylate (GPDM). In various embodiments, the chelating monomer is used in an amount effective to enhance adhesion of the resulting curable mixture to a surface of a tooth.

In one embodiment of an obturation material, component (a) comprises a water-soluble monomer mixture that comprises any two or more of a water-soluble acrylate-based monomer, a water-soluble acrylamide-based monomer, and a water-soluble chelating monomer. For example, component (a) may comprise a water-soluble monomer mixture that comprises a water-soluble acrylate monomer and a water-soluble acrylamide-based monomer. In another embodiment of an obturation material, component (a) comprises a water-soluble monomer mixture that comprises two water soluble acrylate monomers, such as a water-soluble diacrylate monomer and a water-soluble triacrylate monomer.

Various radiopaque materials and mixtures thereof are suitable for use in the curable mixture of ingredients. In some embodiments, the radiopaque material comprises at least one of a polymerizable radiopaque monomer or radiopaque salt. The radiopaque material may be water-soluble, such as a water-soluble radiopaque monomer or a water-soluble radiopaque salt. In some embodiments, the radiopaque material is an iodophenyl functionalized polyethylene glycol monomer. The radiopaque salt may be a radio-dense iodide or barium salt, such as calcium iodide, potassium iodide, sodium iodide, barium sulfate or barium chloride. In other embodiments, radiopaque salts may include (MRI) radio-contrast agents such as a gadolinium salt and/or a sodium diatrizoate type agent (such as sodium diatrizoate hydrate). Other radiopaque materials include, but are not limited to, radiopaque aromatic acids, such as a water soluble radiopaque aromatic acid derived (meth)acrylate, 5-acrylamido-2,4,6-triiodo isophthalic acid, or diatrizoate sodium hydrate. The radiopaque material may be included in the curable mixture in an amount effective to render the resulting cured mixture radiopaque, e.g., suitable for imaging by dental X-ray. The radiopacity of cured polymer materials described herein may be measured by ISO6876: 2012, and in some embodiments, have a radiopacity greater than 1 mmAl, or greater than 2 mmAl, or greater than 3 mmAl. In some embodiments, the radiopaque material also acts as a nanofiller material.

In various embodiments of the curable mixture, the ingredients (a), (b) and (c) are dissolved and/or dispersed in the ingredient (d), an aqueous carrier such as water, or a buffer. In some embodiments, the aqueous carrier comprises a buffer that is selected to maintain the pH in the range of about 7.0 to about 8.4. In other embodiments, the buffer is selected to maintain the pH in the range of about 7.2 to about 8.2, or in the range of about 7.4 to about 8.0. In some embodiments, the curable mixture comprises between 10 wt % and 60 wt %, or between 15 wt % and 60 wt %, or between 15 wt % and 50 wt %, or between 20 wt % and 60 wt %, or between 24 wt % and 60 wt %, of the aqueous carrier. In some embodiments, the curable mixture comprises, or comprises about, 5 wt %, 10 wt %, 15 wt %, 20 wt %, 24 wt %, 25 wt %, 30 wt %, 40 wt %, 50 wt %, 60 wt %, 70 wt % or 100 wt % of the aqueous carrier, or any range of values therebetween.

Free-radical polymerization initiators suitable for use in the curable mixtures described herein include a halogen molecule, azo compound, organic peroxide, an inorganic peroxide, or other free-radical polymerization initiators. An example of a halogen molecule is Cl2, which forms two radicals upon irradiation with ultraviolet light (UV). An azo polymerization initiator may include, but is not limited to, a diazo free radical initiator such as 2,2'-azobis (2-methylpropionamidine) dihydrochloride (AAPH), 2,2'-azobis[2-(2-imidazolin-2-yl)propane] dihydrochloride (AIPH), azobisisobutyronitrile (AIBN) and 1,1'-azobis-(cyclohexanecarbonitrile) (known as ABCN or ACHN), which yield isobutyronitrile and cyclohexanecarbonitrile radicals, respectively, for example, when heated and/or UV irradiated. Examples of organic peroxides include di-tert-butyl peroxide (tBuOOtBu), which forms t-butoxy radicals when heated and/or UV irradiated, and cumene hydroperoxide (CHP). Examples of inorganic peroxides include peroxydisulfate salts such as potassium persulfate. Free-radical polymerization co-initiators suitable for use herein may include thiosinamine, N-phenylglycine, 2-pyrrolidinone, dimethylaminoethyl acrylate (DMAEA), triethanolamine (TEOA), 1-vinyl-2-pyrrolidone and L-arginine. In some embodiments, the free radical initiator may be present in about 0.1 wt % to about 3 wt %, or about 0.1 wt % to about 2.5 wt %, or 0.2 wt % to about 1.0 wt % based on the total weight of the curable mixture. In other embodiments, the reaction mixture may comprise about 0.2 wt % to 6 wt %, or about 0.2 wt % to 1.5 wt % of a co-initiator. In some embodiments, the free radical initiator may be present in, or in about, 0.1 wt %, 0.2 wt %, 1 wt %, 1.5 wt %, 2.5 wt %, 3 wt %, 6 wt % or 10 wt % based on the total weight of the curable mixture, or any range of values therebetween. In other embodiments, the reaction mixture may comprise, or comprise about, 0.1 wt %, 0.2 wt %, 0.5 wt %, 1 wt %, 1.5 wt %, 2 wt %, 4 wt %, 6 wt % or 10 wt % of a co-initiator, or any range of values therebetween.

In an embodiment of a two-part, self-curing or chemical curing composition, a free-radical polymerization initiator and co-initiator are each included in an amount effective to polymerize the acrylate-based, acrylamide-based and/or water-soluble chelating monomer in the curable mixture to form a cured mixture having properties suitable for use as a tooth filling. The curable mixture may polymerize in the range of about 20° C. to about 40° C., thus allowing convenient curing at temperatures in the range of about room temperature to about physiological temperature.

In some embodiments, a heat curable mixture comprising a free-radical polymerization initiator, such as 2,2'-azobis [2-(2-imidazolin-2-yl) propane] dihydrochloride (AIPH/VA-044) is polymerizable around physiological temperature, thus allowing the mixture to cure in situ upon injection into the tooth space. In a further embodiment, light curable compositions are polymerizable, for example, upon exposure to a dental curing light with light energy at a λmax wavelength between 400 nm and 500 nm. Light initiators suitable for use herein include, but are not limited to, 2,2'-azobis[2-methyl-N-(2-hydroxyethyl)propionamide (AMPH/VA-086), camphorquinone (CQ), 1-phenyl-1,2-propanedione (PPD), 7,7-dimethyl-2,3-dioxobicyclo[2.2.1] heptane-1-carboxylic acid (CCQ), and mixtures thereof. Light co-initiators may include, but are not limited to N-phenylglycine, 2-pyrrolidinone, dimethylaminoethyl acrylate (DMAEA), 1-vinyl-2-pyrrolidone, triethanolamine (TEOA), L-arginine, and mixtures thereof.

In some embodiments, a dual curable mixture is provided that comprises both a light initiator and a heat initiator that may be cured through sequential exposure to light energy and heat energy. In one embodiment, after filling a tooth space the dual curable mixture may be partial cured upon exposure to light energy, for example, to prevent or reduce movement of a low viscosity material out of the tooth. However, where the light energy may not penetrate beyond a certain depth or into nonlinear or side canals, the obturation material may be further cured through exposure to heat, such as physiological temperature.

A method is provided for forming a cured mixture within a tooth space by positioning a curable mixture within the tooth space, initiating a first curing reaction by exposing the curable mixture to a first energy source to render the curable mixture substantially stable, and initiating a second curing reaction by exposing the stable curable mixture to a second energy source to form the cured material.

In some embodiments, the curable mixture further comprises a polymerization cross-linker. Various polymerization cross-linkers are suitable for use in the curable mixture of ingredients. In some embodiments, the polymerization cross-linker is an acrylate monomer, a polyacrylate monomer, a polymethacrylate ester monomer, or a mixture thereof. In some embodiments, the polymerization cross-linker is of a low molecular weight relative to the water-soluble acrylate-based monomer. Examples include N,N'-methylenebis(acrylamide) (MBAA), triethylene glycol dimethacrylate (TEGDMA), PEG diacrylate (e.g., with Mn 200), ethylene glycol diacrylate, triethylene glycol-bis-methacrylate, ethylene glycol-dimethacrylate, triethyleneglycol-bis-acrylate, 3,3'-ethylidene-bis (N-vinyl-2-pyrrolidone), trimethylolpropane trimethacrylate, pentaerythritol triacrylate, glycerol trimethacrylate, polyethylene glycol dimethacrylate, trimethylolpropane ethoxylate triacrylate, di(trimethylolpropane) tetraacrylate, pentaerythritol tetraacrylate, star shaped 6-arm (TP) PEG-acrylate, 8-arm (TP) PEG-acrylate, or mixtures thereof. In some embodiments, the amount of polymerization cross-linker is, or is approximately 0.005 wt. %, 0.01 wt. %, 0.02 wt. %, 0.03 wt. %, 0.04 wt. %, 0.05 wt. %, 0.06 wt. %, 0.08 wt. %, 0.1 wt. %, 0.12 wt. %, 0.15 wt. %, 0.2 wt. %, 0.3 wt. %, 0.5 wt. %, 0.8 wt. %, 1 wt. %, 1.5 wt. %, 2 wt. %, 2.5 wt. %, 3 wt. % or 5 wt. % of the total weight of the mixture, or any range of values therebetween. For example, in some embodiments the amount of polymerization cross-linker is, or is approximately, 0.02 wt. % to 2 wt. % of the total weight of the mixture, or 0.05 wt. % to 1 wt. %, or 0.5 wt. % to 5 wt. %, of the total weight of the mixture. In some embodiments, the amount of polymerization cross-linker is, or is approximately 0.05 wt. %, 0.06 wt. %, 0.08 wt. %, 0.1 wt. %, 0.12 wt. %, 0.15 wt. %, 0.2 wt. %, 0.3 wt. %, 0.5 wt. %, 0.8 wt. %, 1 wt. %, 1.5 wt. %, 2 wt. %, 2.5 wt. %, 3 wt. %, 4 wt. %, 5 wt. %, 6 wt. %, 7 wt. %, 8 wt. %, 10 wt. %, 12 wt. %, 15 wt. % or 20 wt. % of the total amount of monomer (i.e. acrylate-based monomer, acrylamide-based monomer, chelating monomer and polymerization cross-linker), or any range of values therebetween. For example, in some embodiments the amount of polymerization cross-linker is, or is approximately, 0.1 wt. % to 10 wt. % of the total amount of monomer, or 1 wt. % to 8 wt. % of the total amount of monomer. In some embodiments, the weight ratio of polymerization cross-linker to monomer is, or is approximately, 1:100, 1:75, 1:60, 1:50, 1:40, 1:30, 1:20, 1:15, 1:10 or 1:5, or any range of values therebetween. For example, in some embodiments the weight ratio of polymerization cross-linker to total amount of monomer is, or is approximately, 1:50 to 1:10, or 1:30 to 1:15.

In some embodiments, the curable mixture further comprises an acid, such as an acid monomer, suitable for use in the curable mixture. In some embodiments, the acid monomer is an acrylic acid. Examples include methacrylic acid, acrylic acid, methacryloyloxyethyl succinate, or mixtures thereof. Acid monomers that increase the hydrophilicity and/or provide crosslinking sites may be suitable for use in making hydrogel polymers for use as obturation materials. In some embodiments, the amount of the acid monomer may be between 0.1 wt % and 0.5 wt %, or between 0.2 wt % and 0.3 wt %, based on the total weight of the curable mixture. In some embodiments, the amount of the acid monomer may be, or be about, 0.1 wt %, 0.2 wt %, 0.3 wt %, 0.4 wt %, 0.5 wt %, 0.7 wt % or 1 wt % based on the total weight of the curable mixture, or any range of values therebetween.

In some embodiments, the curable mixture further comprises an antimicrobial or antibacterial reagent. Various antimicrobial reagents are suitable for use in the curable mixture of ingredients. Examples include, but are not limited to, zinc oxide, (3-acrylamidolpropyl)trimethyl-ammonium chloride (APTA), [2-(acryloyloxy)ethyl]trimethyl-ammonium chloride (EGAA-QCl), or mixtures thereof. When present, the amount of the acid monomer may be between 0.5 wt % and 2.5 wt %, based on the total weight of the curable mixture.

In some embodiments, obturation materials formed from curable materials disclosed herein may reduce the amount of harmful bacteria for *Eschericia coli* (*E. coli*). *Enterococcus faecalis* (*E. faecalis*), or both. In some embodiments, materials described herein may demonstrate at least a 1 log reduction, or at least a 2 log reduction, from the initial count of *E. coli*, *E. faecalis*, or both, when tested in an initial biofilm study according to USP <51> Antimicrobial Effectiveness Testing.

In some embodiments, the curable mixture further comprises a surfactant. Various surfactants are suitable for use in the curable mixture of ingredients. Examples include Triton X-100.

In some embodiments, the curable mixture further comprises an inhibitor. Various inhibitors are suitable for use in the curable mixture of ingredients. Examples include 4-methoxyphenol (MEHQ), hydroquinone (HQ) and 2,6-di-tert-butyl-4-methyl phenol (BHT). In various embodiments the inhibitor is used in an amount effective to slow the curing time of the curable mixture.

In various embodiments, at least a portion of the curing of the curable mixture takes place after positioning the curable mixture in a cavity or root canal. For example, an embodiment provides a method of filling a tooth, comprising identifying a tooth having a cavity in need of filling; positioning a curable mixture as described herein within the cavity; and curing the curable mixture within the cavity. Another embodiment provides a method of filling a tooth, comprising identifying a tooth having a root canal in need of filling; positioning a curable mixture as described herein within the root canal; and curing the curable mixture within the root canal. The positioning of the curable mixture in the cavity or root canal can be carried out in various ways as described elsewhere herein. In a further embodiment, a method comprises providing a curable obturation material in at least two parts, wherein each part of the curable material is a liquid that is delivered separately to a handheld device, for example, through first and second ports of the handheld device. In an embodiment, the handheld device comprises a liquid jet, and first and second solutions of a two-part curable obturation material are provided through first and second ports of the handheld device. The first and second parts are then mixed to form a curable obturation material by the liquid jet prior to filling a tooth space, wherein the curable obturation material cures to form a solid hydrogel.

Optionally, the curable obturation material is degassed prior to mixing the first and second solutions. The percent reduction of dissolved gas (for example, mg/L dissolved oxygen) may be at least 10% after degassing. Optionally, a first part, second part and/or the curable obturation reaction mixture have a viscosity less than 60 cP, or less than 40 cP, or less than 30 cP or less than 20 cP, at ambient conditions (approximately 25° C.), for example, when measured on a Brookfield viscometer. In one embodiment of a curable obturation material, a first liquid part comprises a viscosity less than 60 cP (at approx. 25° C.) and a second part comprises a viscosity less than 20 cP (at approx. 25° C.), prior to mixing in a handpiece.

To protect the root canal from infection over time, an obturation material may be resistant towards degradation. In some embodiments, a durable cured obturation material comprises hydrogel having a hardness greater than 20 Shore A, or greater than 60 Shore A, or greater than 70 Shore A, or between 20 Shore A and 90 Shore A. Hydrogel obturation materials may exhibit low volumetric shrinkage upon curing and low diametral swelling upon curing. In one embodiment, cured obturation materials provided herein have a diametral swelling is less than 40%.

Application Device

The curable obturation materials and cured obturation materials described herein may be applied to a tooth by various methods and devices. The filling or obturation material may be formed in any suitable manner. For example, in some embodiments, a clinician can form the obturation material by mixing the obturation material ingredients, e.g., by hand, by a mechanical tool, or by a mixing device. Furthermore, the obturation material can be applied to a tooth in any suitable manner. For example, in some embodiments, a clinician may apply the obturation material in the tooth, e.g., by hand, syringe, mechanical tool, or application device. In FIGS. 1 through 2B, embodiments of a mixing device and/or an application device that can be used to form and/or apply an obturation material are disclosed. In some embodiments, a clinician can form the obturation material by mixing the obturation material ingredients outside of an application device, place the obturation material into an application device, and apply the obturation material to a tooth using the application device. A composition consisting of all the ingredients of the curable mixture except for at least one missing ingredient may be loaded into an application device, and the composition and the missing ingredient may be combined within the application device to form the obturation material, and the obturation material is applied to a tooth using the application device.

FIG. 1A is a schematic diagram of a system 1, in accordance with embodiments of an application or delivery device as disclosed herein. The system 1 can be configured to perform various types of treatment procedures, including, e.g., cleaning treatments, obturation or other filling treatments, restoration treatments, etc. In the embodiment shown in FIG. 1A, the system 1 is illustrated as being coupled to (e.g., positioned against in some arrangements) a tooth 10 that is a molar tooth of a mammal, such as a human. However, the tooth 10 can be any other suitable type of tooth, such as a pre-molar, bicuspid, incisor, canine, etc. Furthermore, the system 1 shown in FIG. 1A can include components configured to remove unhealthy or undesirable materials from a tooth or surrounding gum tissue, for example, a root canal 13 of the tooth 10. Thus, in the embodiment of FIG. 1A, the system 10 can also be configured to clean the tooth 10, in addition to being configured to fill or obturate the tooth. Moreover, although the treatment shown in FIG. 1A is a root canal treatment, in other embodiments, the application device and obturation material(s) disclosed herein can be used to fill other types of treatment regions, such as a treated carious region of the tooth.

The tooth 10 includes hard structural and protective layers, including a hard layer of dentin 16 and a very hard outer layer of enamel 17. A pulp cavity 11 is defined within the dentin 16. The pulp cavity 11 comprises one or more root canals 13 extending toward an apex 14 of each root 12. The pulp cavity 11 and root canal 13 contain dental pulp, which is a soft, vascular tissue comprising nerves, blood vessels, connective tissue, odontoblasts, and other tissue and cellular components. Blood vessels and nerves enter/exit the root canal 13 through a tiny opening, the apical foramen or apical opening 15, near a tip of the apex 14 of the root 12. It should be appreciated that, although the tooth 10 illustrated herein is a molar, the embodiments disclosed herein can advantageously be used to treat any suitable type of tooth, including pre-molars, canines, incisors, etc.

The system 1 can include a console 2, a pressure wave generator 5, and a tooth coupler 3 (such as a handpiece) adapted to couple to the tooth 10. The tooth coupler 3 can couple to the tooth 10 in any suitable way. In some arrangements, the tooth coupler 3 can be positioned against and/or attach to the tooth 10 by way of a tooth seal 75. For example, the clinician can hold the tooth coupler 3 against the tooth 10 during treatment. In some embodiments, the tooth coupler 3 can define a chamber 6 configured to retain fluid therein, such as a filler or obturation material described herein. In some embodiments, the pulp cavity 11 can define a tooth chamber configured to retain fluid therein. In some embodiments, the tooth coupler 3 may not define a chamber, and the tooth chamber defined at least in part by the pulp cavity 11 can retain fluid.

The tooth coupler 3 disclosed herein can be any suitable structure or housing configured to couple to the tooth 10 for a treatment procedure. As used herein, "couple" is meant to include arrangements in which there is a connection with the tooth 10, as well as arrangements in which the coupler 3 is placed against or in the tooth and is held by the clinician in that position. The pressure wave generator 5 can be coupled to and/or disposed in or on the tooth coupler 3 in various embodiments.

A system interface member 4 can electrically, mechanically, and/or fluidly connect the console 2 with the tooth coupler 3 and pressure wave generator 5. For example, in some embodiments, the system interface member 4 can removably couple the tooth coupler 3 to the console 2. In such embodiments, the clinician can use the tooth coupler 3 one time (or a few times) and dispose of the tooth coupler 3 after each procedure (or after a set number of procedures). The console 2 and interface member 4 can be reused multiple times to removably couple (e.g., to connect and/or disconnect) to multiple tooth couplers 3 using suitable engagement features, as discussed herein. The interface member 4 can include various electrical and/or fluidic pathways to provide electrical, electronic, and/or fluidic communication between the console 2 and the tooth coupler 3. The console 2 can include a control system and various fluid and/or electrical systems configured to operate the pressure wave generator 5 during a treatment procedure. The console 2 can also include a management module configured to manage data regarding the treatment procedure. The console 2 can include a communications module configured to communicate with external entities about the treatment procedures. Additionally, the console 2 can include a control system comprising a processor and non-transitory memory. Computer-implemented instructions can be stored on the memory and can be executed by the processor to assist in controlling cleaning and/or filling procedures. Additional details of the console 2 can be found in U.S. Pat. No.

9,504,536, and in U.S. Pat. No. 9,675,426, each of which is incorporated by reference herein in its entirety and for all purposes.

In FIG. 1A, the system 1 is used to fill or obturate the root canal 13 with an obturation material 45, which can be the same as, or generally similar to, the filler materials described herein. When the root canal 13 is cleaned, the clinician can supply an obturation material 45 in a flowable state to the pulp cavity 11, canals 13, or other internal chambers of the tooth 10. In some embodiments, a pressure wave generator 5 may be coupled to, or formed with, a handpiece having one or more openings configured to deliver the flowable obturation material 45 to the tooth 10. In still other embodiments, a dental handpiece may include one or more supply lines to supply the flowable obturation material 45 to the tooth 10. An obturation material 45 may have a first state which is flowable, to flow through the treatment region to fill the root canals 13 and/or pulp cavity 11. The obturation material 45 may harden to form a second state by solidifying after filling the treatment region.

Advantageously, the pressure wave generator 5 can be activated to assist in positioning the obturation material 45 throughout the treatment region to be filled, thereby assisting in substantially filling the tooth 10. As shown in inset 50 of FIG. 1A, for example, when activated, the pressure wave generator 5 may cause the obturation material 45 to flow into major canal spaces 51 of the tooth 10, as well as into small spaces 53 of the tooth 10. Thus, the system 1 shown in FIG. 1A can assist in filling small cracks, tubules, and other tiny spaces (e.g., the small spaces 53) of the tooth 10. By filling the small spaces 53 of the tooth, the system 1 can ensure a more robust obturation procedure which results in long-term health benefits for the patient. The pressure waves 23 and/or fluid motion 24 (which can include vortices 74) generated by the pressure wave generator 5 can interact with the obturation material 45 to assist in filling the small spaces 53 and the major spaces 51 of the tooth 10. Furthermore, in some embodiments, the pressure wave generator 5 can be activated to assist in curing or hardening the obturation material 45. In some embodiments, curing or hardening of the obturation materials may be enhanced when agitated by pressure waves 23 generated by the pressure wave generator 5.

Obturation or filling material may be degassed to facilitate delivery of the obturation material to spaces of the tooth. In some embodiments, presence of dissolved gas in an obturation material may result in bubbles that block, or inhibit, the transfer or flow of, the obturation material and/or pressure waves into spaces within a tooth. Upon curing the obturation material, portions of a tooth space or root canal that have not been filled with obturation material may be visualized, for example, by conventional dental X-ray analysis. Where the one or more parts of a reaction mixture solution, or the reaction mixture solution itself, are degassed prior to penetration into the tooth, fewer bubbles may come out of a solution, and a degassed composition may substantially and/or completely penetrate non-linear or small spaces, for example, having a diameter smaller than 500 microns, or smaller than 100 microns, or smaller than 10 microns. In some embodiments, the degassed composition may substantially and/or completely penetrate non-linear or small spaces having a diameter of, of about, less than, or less than about, 1000 microns, 500 microns, 100 microns or 10 microns, or any range of values therebetween.

As used herein, a degassed composition has a dissolved gas content that has been reduced after a degassing step. In some embodiments, dissolved gas content may be reduced by approximately 1% to 70%, or reduced by 5% to 50%, or reduced by 10% to 40%. In some embodiments, dissolved gas content may be reduced by, or by approximately, 1%, 5%, 10%, 20%, 40%, 50%, 70% or 80%, or any range of values therebetween. In some embodiments, the amount of dissolved gas in the liquid compositions before or after degassing may be measured in terms of the amount of dissolved oxygen (e.g., mg/L), for example, by titration, or optical or electrochemical sensors that perform a dissolved gas analysis, such as Pro-Oceanus GTD-Pro or HGTD dissolved gas sensor available from Pro-Oceanus Systems Inc. (Nova Scotia, Canada), or D-Opto dissolved oxygen sensor available from Zebra-Tech Ltd. (Nelson, New Zealand). A degassing step may include known degassing techniques or combinations of thereof, such as heating, helium sparging, vacuum, filtering, de-bubbling, sonication, and the like. In one embodiment, after degassing the curable reaction mixture has an oxygen concentration of 0 mg/L to 3.2 mg/L, when measured using a dissolved oxygen meter.

In some embodiments, the obturation material 45 is supplied to the tooth 10, and the pressure wave generator 5 is subsequently activated to enhance the obturation procedure (e.g., to improve the filling process and/or to enhance or activate the curing process). Sequentially, the clinician may supply the obturation material 45 to the tooth 10 using a syringe or other device, and the pressure wave generator 5 may subsequently (or concurrently) be activated to fill the treatment region. In other embodiments, the pressure wave generator 5 may supply the obturation material 45 and generate pressure waves through the obturation material (or other fluids at the treatment region) simultaneously, or the steps of supplying the obturation material to the tooth and filling the tooth by generating pressure waves within the tooth, may overlap in time. For example, where the pressure wave generator 5 comprises a liquid jet, a jet of obturation through obturation materials in the treatment region. Interaction of the fluid jet and the obturation material can enhance the obturation procedure.

As disclosed herein, a pressure wave generator 5 comprises any suitable wave generator, including but not limited to a liquid jet device, a laser, a mechanical stirrer, and an ultrasonic transducer. The pressure wave generator 5 may be disposed outside the region of the tooth 10, having a chamber 6 disposed outside the tooth 10. In other arrangements, a pressure wave generator 5 extends partially into the tooth 10. In some arrangements, the pressure wave generator 5 can extend to a depth that does not interfere with the filling. The system 1 can include a cleaning mode for cleaning the treatment region and a filling mode to fill or obturate the treatment region. The console 2 can include a control system comprising a processor and memory. The control system can be programmed or configured to switch the system 1 from the cleaning mode to the filling mode and vice versa. The control system of the console 2 can also control the operation of cleaning and/or filling procedures. Additional details of the delivery device shown in FIG. 1A can be found throughout U.S. Pat. No. 9,877,801, the entire contents of which are incorporated herein by reference and particularly for the purpose of describing such details.

Figure 1B:
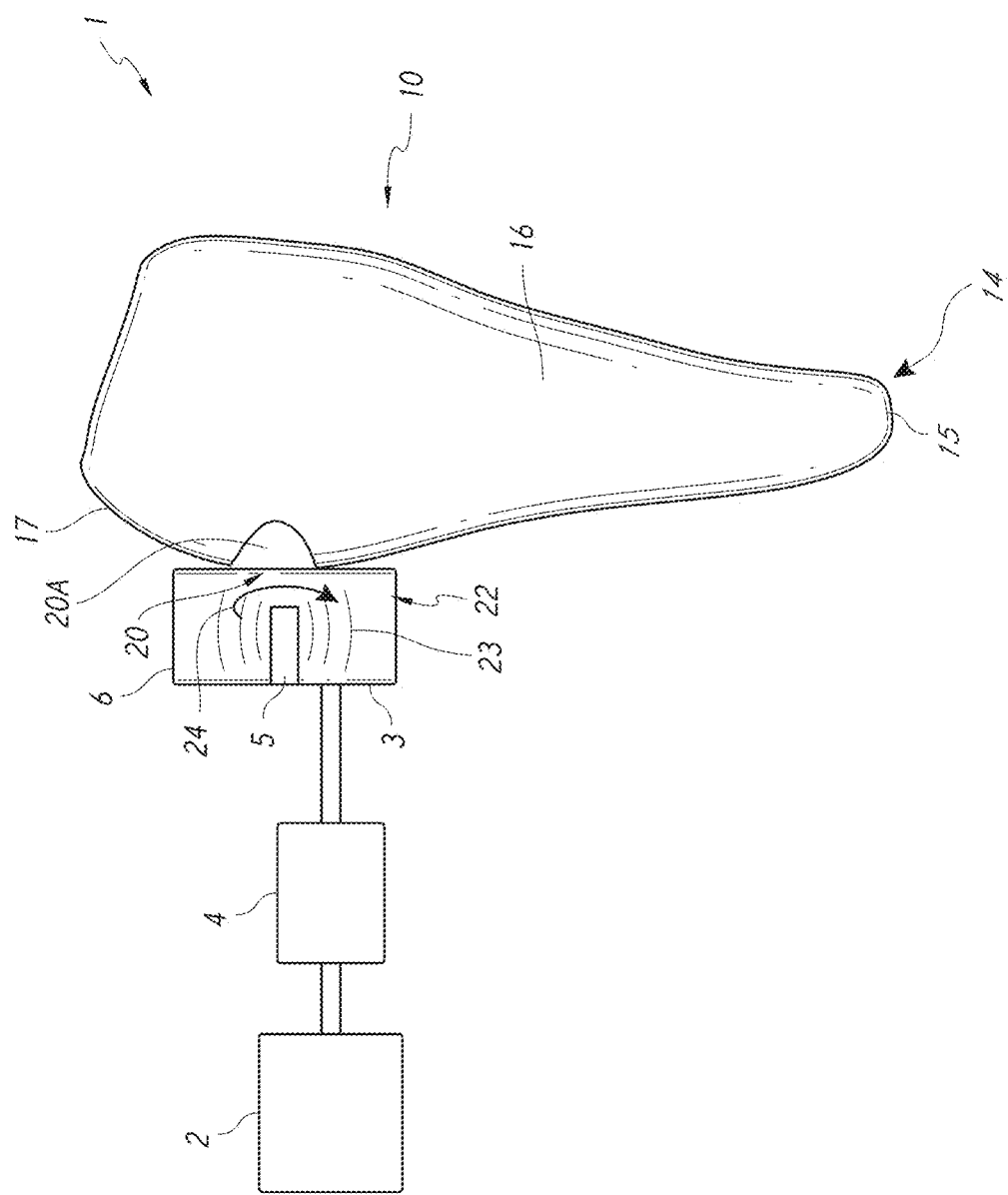
FIG. 1B is a schematic diagram of a system that includes components configured to clean unhealthy or undesirable material from a treatment region on an exterior surface of the tooth.

FIG. 1B is a schematic diagram of a system 1 that includes components configured to clean unhealthy or undesirable material from a treatment region 20 on an exterior surface of the tooth 10. For example, as in FIG. 1A, the system 1 can include a tooth coupler 3 and a pressure wave generator 5. The tooth coupler 3 can communicate with a console 2 by way a system interface member 4. Unlike the system 1 of FIG. 1A, however, the tooth coupler 3 is coupled to (e.g., positioned against by a clinician) a treatment region 20 on an exterior surface of the tooth 10. In some embodiments, the tooth coupler 3 can be stably positioned against the treatment region and can be sealed to the tooth 10, e.g., by way of an adhesive or other seal. The system 1 of FIG. 1B can be activated to clean an exterior surface of the tooth 10, e.g., a carious region of the tooth 10 and/or remove undesirable dental deposits, such as plaque, calculus biofilms, bacteria, etc, from the tooth 10 and/or surround gum tissue. In other embodiments (see FIG. 1C), the system 1 can be activated to fill a treated region on the exterior surface of the tooth 10 with a filling or restoration material. As with the embodiment of FIG. 1A, pressure waves 23 and/or fluid motion 24 can be generated in the tooth coupler 3 and chamber 6, which can act to clean the treatment region 20 of the tooth 10, forming a cleaned treatment region 20A in which the carious (or other unhealthy material) is removed. Additional details of systems and methods for treating carious regions of teeth can be found in International Application Publication WO 2013/142385 (PCT/US2013/032635), having an international filing date of Mar. 15, 2013, entitled "APPARATUS AND METHODS FOR CLEANING TEETH," the entire contents of which are incorporated by reference herein in their entirety and for all purposes. Additional details of systems and methods for removing undesirable dental deposits (such as plaque, calculus, etc.) from teeth and/or gums can be found in International Application Publication WO 2013/155492 (Application No. PCT/US2013/036493), having an international filing date of Apr. 12, 2013, entitled "APPARATUS AND METHODS FOR CLEANING TEETH AND GINGIVAL POCKETS," and in U.S. Patent Publication No. US 2014/0099597, filed Apr. 11, 2013, entitled "APPARATUS AND METHODS FOR CLEANING TEETH AND GINGIVAL POCKETS," each of which is incorporated by reference herein in its entirety and for all purposes.

Figure 1C:
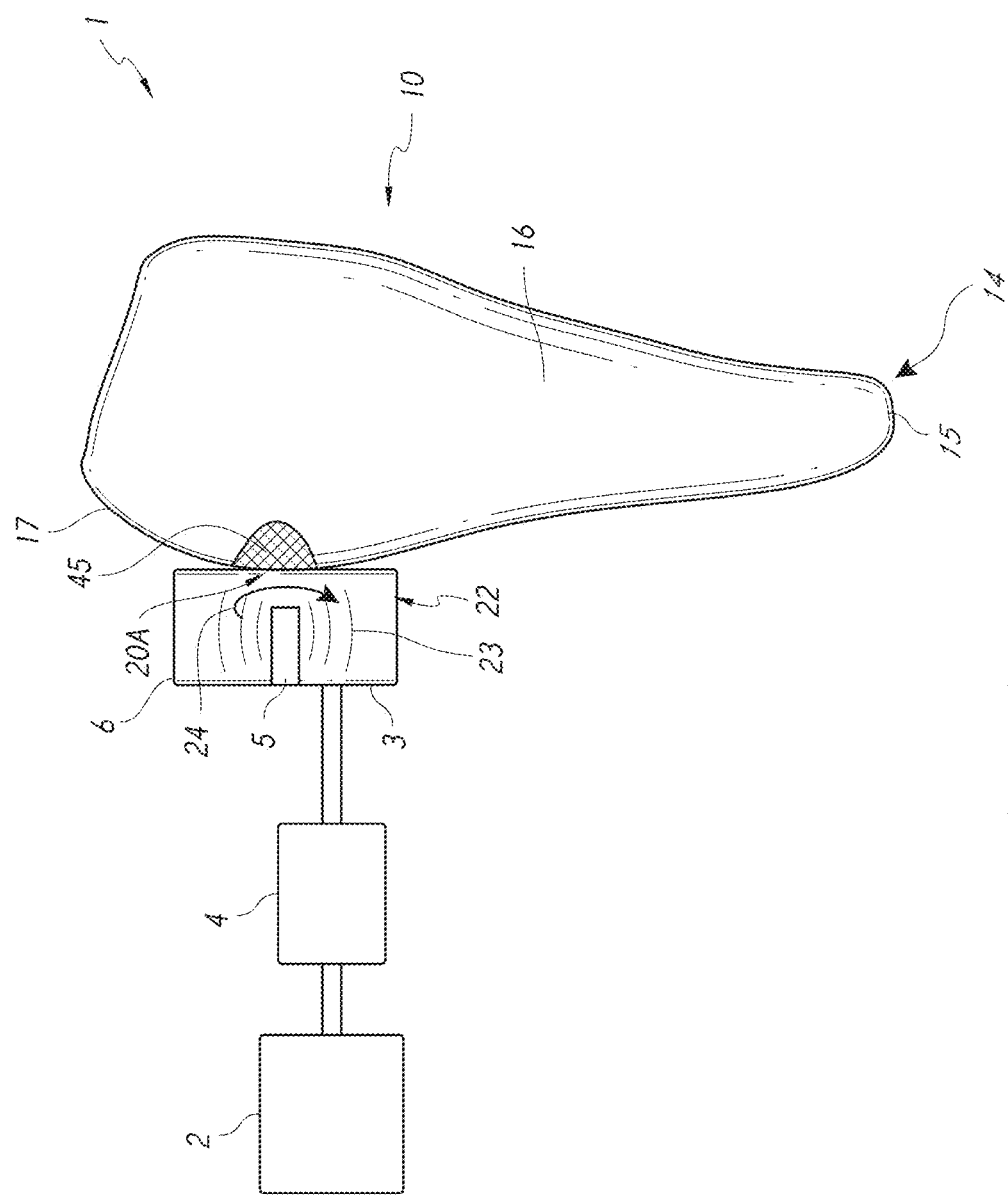
FIG. 1C is a schematic diagram of the system of FIG. 1B, in which the system is configured to fill a treated carious region of the tooth.

FIG. 1C is a schematic diagram of the system 1 of FIG. 1B, in which the system 1 is configured to fill the treated carious region 20A of the tooth 10, and can be used in combination with any of the filling materials disclosed herein. As with the embodiment of FIG. 1B, the system can include a pressure wave generator 5, a tooth coupler 3, an interface member 4, and a console 2. When the carious or other unhealthy material is removed from the tooth 10, the clinician can fill the cleaned treatment region 20A with a suitable filler or obturation material 45. As with the embodiment of FIG. 1A, the obturation material 45 can be supplied to the cleaned treatment region 20A. The pressure wave generator 5 can act to substantially fill the treatment region 20A and/or to enhance or activate the hardening of the filler obturation material 45. In some embodiments, the filler or obturation material 45 is supplied to the tooth 10, and the pressure wave generator 5 is subsequently activated to enhance the filling procedure (e.g., to improve the filling process and/or to enhance or activate the curing process). For example, in such embodiments, the clinician can supply the filler or obturation material 45 to the treatment region 20A using a syringe, and the pressure wave generator 5 can subsequently be activated to fill the treatment region. In other embodiments, the pressure wave generator 5 is activated to supply the filler or obturation material 45 to the treatment region 20A and to generate pressure waves through the material. For example, in embodiments in which the pressure wave generator 5 comprises a liquid jet, a jet of obturation or filler material 45 (or other type of fluid) can interact with fluids at the treatment region 20A (e.g., other portions of the filler or obturation material or other treatment fluid) to generate pressure waves that propagates through the fluids. The resulting pressure waves can enhance the obturation procedure.

Figure 2A:
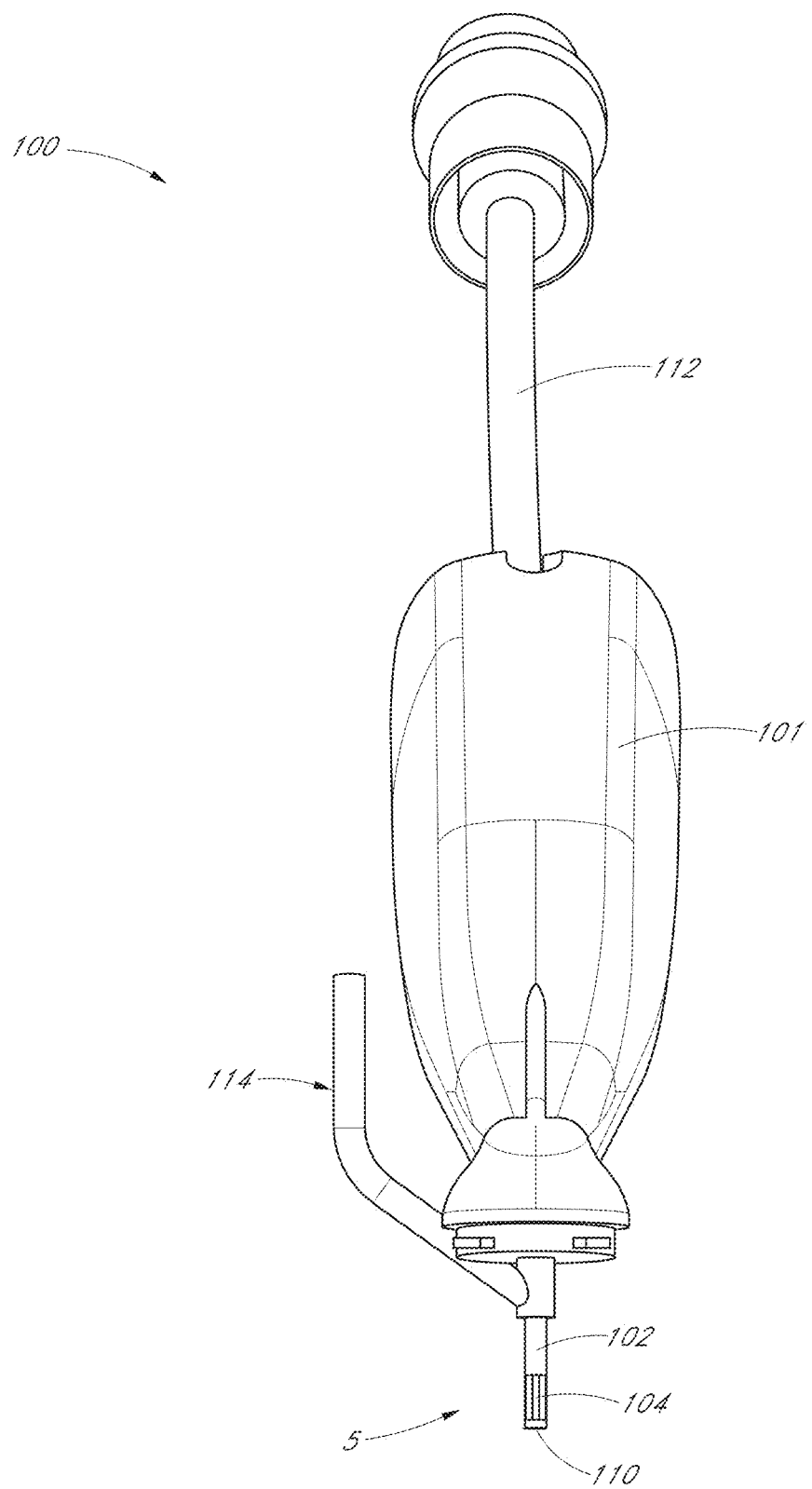
FIG. 2A is a schematic top plan view of a delivery device that can be used to combine a first composition with a second composition to form a curable mixture and to fill a treatment region.
Figure 2B:
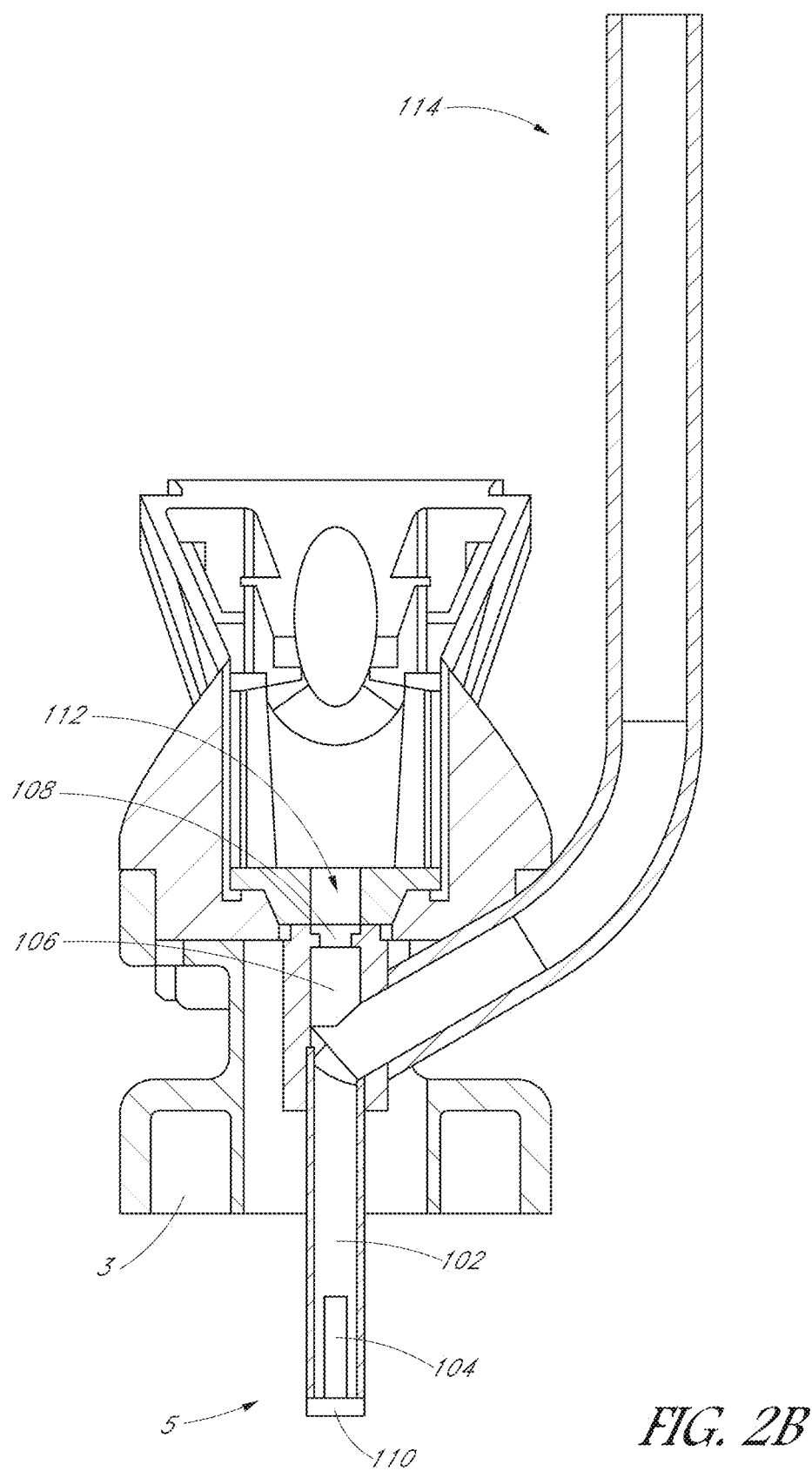
FIG. 2B is a schematic side sectional view of a portion of the delivery device of FIG. 2A.

FIGS. 2A and 2B depict a delivery device 100 that can be used to combine a first composition with a second composition to form the curable mixture and apply it to a treatment region of the tooth to fill the treatment region. As shown in FIGS. 2A-2B, the delivery device 100 can comprise a treatment instrument 101. The treatment instrument 101 can be used to position the pressure wave generator 5 at or near the treatment region. In the embodiment of FIG. 2A, the treatment instrument 101 comprises a handpiece sized and shaped to be held by the clinician against a portion of the tooth. Further, the delivery device 100 can comprise a first composition supply line 112 and a second composition supply line. The first composition supply line 112 can be configured to supply the first composition to a distal portion of the handpiece 101. The second composition supply line 114 can be configured to supply the second composition to the distal portion of the handpiece 101. For example, in some embodiments, the first composition line 112 can be configured to supply the carrier liquid to the tooth, and the second composition 114 can supply other component materials to mix with the carrier liquid.

In FIG. 2A, a pressure wave generator 5 can be coupled to or formed with the distal portion of the handpiece 101. As explained above in connection with FIG. 1A through FIG. 1C, the pressure wave generator 5 can be activated to generate pressure waves and/or fluid motion at the treatment region, to cause the filling or obturation material to fill the treatment region. As explained above, the pressure wave generator 5 can comprise any suitable type of pressure wave generator, including those described in U.S. Pat. No. 9,877,801, the entire contents of which are incorporated herein by reference in their entirety and for all purposes. For example, the pressure wave generator 5 of FIGS. 2A-2B comprises a liquid jet device. The liquid jet device can comprise a nozzle or orifice 108 sized and shaped to pressurize the first composition that is supplied to the orifice 108 by way of the first composition supply line 112. In some embodiments, the orifice 108 can form the first composition into a liquid jet, e.g., a coherent, collimated liquid jet. The liquid jet formed of the first composition can pass into a mixing chamber 106 disposed distal the orifice 108. Thus, in FIG. 2B, the second supply line 114 can be positioned to deliver the second composition to the mixing chamber 106 at a location distal the orifice 108. Thus, the liquid jet of, for example, the carrier material, can be formed and can pass through the mixing chamber 106 to interact with other component materials of a curable obturation material supplied by the second supply line 114.

As shown in FIG. 2B, the second composition supply line 114 can supply the second composition to the mixing chamber 106 by way of one or more ports. The first and second compositions can accordingly be mixed within the mixing chamber 106 to at least partially form the mixed composition of the filling or obturation material. The momentum of the liquid jet can drive the at least partially mixed first and second compositions along a guide tube 102. The liquid jet can impinge on an impingement member 110 located at a distal portion of the guide tube 102. The delivery device 100 can comprise a side port delivery device in which the curable mixture is supplied to the treatment region through one or a plurality of openings 104 in the guide tube 102. The openings 104 can be disposed proximal the impingement member 110. Interaction of the at least partially mixed first and second compositions with fluid in the treatment region can generate pressure waves and/or fluid motion at the treatment region. The pressure waves and/or fluid motion can assist in filling or obturating the treatment region. Additional details of liquid jet devices used for filling a treatment region can be found in FIGS. 4A through 8D of U.S. Pat. No. 9,877,801, the entire contents of which are incorporated by reference herein in their entirety and for all purposes.

Accordingly, in some embodiments, the first and second compositions can be kept separate until combined in the mixing chamber 106 of the delivery device 100 to form the curable mixture. For example, in some embodiments, the first or second composition can consist of all the ingredients of the curable mixture except for at least one missing ingredient. In some embodiments, the missing ingredient can be the carrier fluid or a portion of the carrier fluid, whereby combination of the second composition decreases the viscosity of the first composition in order to create a curable mixture suitable for delivery to the treatment region. In some embodiments, the missing ingredient can initiate curing or hardening of the curable obturation material formed when combining the first and second compositions. In some embodiments, at least one of the first and second compositions are introduced into the curable mixture as a fluid jet as explained herein.

Although the examples shown in FIGS. 1-2B describe the delivery device as including a pressure wave generator, it should be appreciated that the obturation material(s) described herein can be used in conjunction with any other suitable type of delivery device. For example, the obturation material(s) described herein can be delivered to the tooth with a syringe, a mechanical instrument, or any other suitable device.

Kits

The curable materials, obturation materials and the application devices described herein can be combined in the form of a kit. In some embodiments, the kit includes a first container comprising a first mixture of a composition consisting of all the ingredients of the curable mixture except for at least one missing ingredient, a second container comprising a second mixture of a composition comprising the missing ingredient, and an application device. In one embodiment, a kit for dispensing a curable hydrogel obturation material comprises 1) a curable obturation mixture provided as two liquid parts, wherein a first liquid part comprises a water soluble acrylate-based polymer, and the second liquid part comprises an initiator, and 2) a handpiece for delivering the curable obturation material to a tooth comprising a first opening for receiving the first liquid part, a second opening for receiving the second liquid part, a mixing chamber, and a nozzle to dispense the mixture into a tooth.

In other embodiments, a kit comprises obturation materials as described herein (for example, the first and second containers described above), and not the application devices. In some embodiments, the elements of the kit are packaged together in a single packaging.

EXAMPLES

Radiopacity

The determination of radiopacity of compositions was tested by reference to a specimen of an aluminum (Al) standard according to ISO 6876:2012.

Leachable

Leachable testing of the materials was determined according to test 5.6—Solubility per ISO 6876:2012 Root Canal Sealing Materials, and calculated as follows:

$$\% \text{ leachable} = \frac{\text{mass of petri dish after} - \text{mass of petri dish before}}{\text{mass of sample 1} + \text{mass of sample 2}} * 100\%$$

Swelling

Diametral swelling was determined by placing material in circular plastic molds with ca. 20 mm diameter and 1.5 mm thickness. Cured samples were measured, and allowed to swell in water for 24 hours at 37° C. The percent of diametral swelling was calculated as follows:

$$\% \text{ diametral swelling} = \left[ \left( \frac{\text{(Area of sample 1 after swelling} - \text{area of mold 1)}}{\text{(area of sample 1 after swelling)}} * 100\% \right) + \left( \frac{\text{(Area of sample 1 after swelling} - \text{area of mold 1)}}{\text{(area of sample 1 after swelling)}} * 100\% \right) \right] / 2$$

To determine percent swelling at 37° C., samples that had been swelling at 37° C. were transferred into a petri dish and heated in 60° C. oven to dry. The mass was measured before and after drying, and calculated as follows:

$$\% \text{ swelling at } 37° \text{ C.} = \frac{\text{(sample 1 swolen} + \text{sample 2 swolen)} - \text{(sample 1 dried} + \text{sample 2 dried)}}{\text{(sample 1 swollen} + \text{sample 2 swollen)}} * 100\%$$

Percent water uptake was calculated as follows:

$$\% \text{ water uptake} = \frac{\text{(sample 1 after swelling} + \text{sample 2 after swelling)} - \text{(sample 1 before swelling} + \text{sample 2 before swelling)}}{2} * 100\%$$

Example 1: Preparation of Buffer Solution

Sodium phosphate dibasic, potassium phosphate monobasic, and potassium chloride were added, in the amounts as indicated by Table 1, into 1 liter water and thoroughly mixed, in a glass beaker, with a stir plate. All the ingredients were fully dissolved to obtain "Buffer Solution". An electronic pH meter indicated a pH value of 7.8.

TABLE 1

| Phosphate Buffer Solution (pH7.8) | |
|---|---|
| Ingredient | Amount |
| sodium phosphate dibasic (Sigma Aldrich ® #S7907-100G) | 1.4196 g (0.14 wt %) |
| potassium phosphate monobasic (Sigma Aldrich ® #S5655-500G) | 0.242 g (0.02 wt %) |
| potassium chloride (Sigma Aldrich ® #P933-500G) | 0.201 g (0.02 wt %) |
| water | 1 kg (99.81 wt %) |

Example 2

A hydrogel obturation material was prepared from a two-part curable mixture comprising aqueous acrylate-based monomer solutions according to Table 2 and Table 3.

TABLE 2

Aqueous Acrylate-based Monomer Solution 1

| Ingredient | Amount |
| --- | --- |
| Poly(ethylene glycol) diacrylate (Sigma Aldrich ® #455008-100ML) | 1 g (4.04 wt %) |
| potassium persulfate (Sigma Aldrich ® #216224-100G) | 0.255 g (1.03 wt %) |
| phosphate buffer Solution (pH 7.8) (made according to Table 1) | 23.5 g (94.93 wt %) |

TABLE 3

Aqueous Acrylate-based Monomer Solution 2

| Ingredient | Amount |
| --- | --- |
| ethoxylated trimethylolpropane triacrylate (Sigma Aldrich ® #412198-250ML) | 13.38 g (49.35 wt %) |
| triethanolamine (Sigma Aldrich ® #90279-100ML) | 0.235 g (0.87 wt %) |
| Phosphate Buffer Solution (pH 7.8) (made according to Table 1) | 13.5 g (49.79 wt %) |

The two-part curable mixture comprised aqueous acrylate-based monomer solutions 1 and 2 ("Solution 1" and "Solution 2"), made according to Tables 2 and 3, respectively. Solution 1 contained the indicated amounts of polyethylene glycol diacrylate, potassium persulfate, and phosphate buffer solution of pH 7.8 prepared in the manner described in Example 1; and Solution 2 contained the indicated amounts of ethoxylated trimethylolpropane triacrylate, triethanolamine as a co-initiator, and phosphate buffer solution of pH 7.8 prepared in the manner described in Example 1.

Solution 1 was heated on a hotplate to 37° C. with constant stirring using a stir bar. After 5 minutes, Solution 2 was mixed with Solution 1 on the hotplate to form a curable mixture. The polymerization initiated and stirring of the mixture during the subsequent cure was continued until the resulting cured mixture was fully cured. The resultant hydrogel appeared white, rubbery and flexible, as a solid block of material. No residue was left behind in the beaker. The hydrogel material could be torn or cut with relative ease. A radiograph was taken, confirming that the cured mixture was not radiopaque.

Example 3

Aqueous acrylate-based Monomer Solution 3 ("Solution 3"), was made according to Table 4. A two-component aqueous acrylate-based obturation material was thereby provided comprising Solution 3, which contained the indicated amounts of polyethylene glycol diacrylate, potassium persulfate, sodium diatrizoate hydrate, and phosphate buffer solution of pH 7.8, and Solution 2, which contained the indicated amounts (Table 2) of ethoxylated trimethylolpropane triacrylate, triethanolamine, and phosphate buffer solution of pH 7.8.

TABLE 4

Aqueous Acrylate-based Monomer Solution 3

| Ingredient | Amount |
| --- | --- |
| Poly(ethylene glycol) diacrylate (Sigma Aldrich ® #455008-100ML) | 1 g (3.81 wt %) |
| Potassium persulfate (Sigma Aldrich ® #216224-100G) | 0.255 g (0.97 wt %) |
| Phosphate Buffer Solution (pH 7.8) (made according to Table 1) | 23.5 g (89.51 wt %) |
| Sodium diatrizoate hydrate (Sigma Aldrich ® #54506-500G) | 1.5 (5.71 wt %) |

Solution 3 was heated on a hotplate to 37° C. with constant stirring. After less than 5 minutes Solution 2 was mixed with Solution 3 on the hotplate. Polymerization was initiated and stirring of the mixture during the subsequent cure was continued until the resulting cured mixture was fully cured. The resultant hydrogel appeared more brittle than the hydrogel as described above herein in Example 2. The hydrogel of Example 3 was able to be crumbled into large chunks. The hydrogel material of Example 3 held together when handled normally and was flexible to an extent. Some moisture was left in the mixing beaker however, no residual hydrogel material of Example 3 was observed. Slight yellow color began to appear on the hydrogel material of Example 3 after sitting in room conditions for some time and maintained the general mechanical properties of flexibility.

A radiograph taken of the hydrogel material of Example 3 showed some radiopacity due to the diatrizoate ingredient included in Solution 3 as described above herein.

Example 4

A hydrogel was made using Solutions 2 and 3, except that an additional 0.25 g of potassium persulfate was included in Solution 3 to accelerate the reaction rate. The hydrogel material of Example 4 appeared similar in mechanical properties to the hydrogel material of Example 1, being flexible and soft while reforming elastically rather than exhibiting plastic deformation.

Examples 5-14

Two-part chemical curing (self-curing) reaction mixtures were prepared comprising aqueous diacrylate and/or triacrylate monomer solutions, initiators and a radiopaque component. The triacrylate was ethoxylated trimethylolpropane triacrylate (ETT, Mn 912), and the diacrylate was poly(ethylene glycol) diacrylate (PEG) Mn 700). The radiopaque agents for Examples 5 through 14 were zinc oxide or barium sulfate.

Curable reaction mixtures were made according to Table 5. For each solution of Examples 5 through 14, all ingredients except the initiators were combined and stirred at ambient temperature to form a first liquid mixture. The initiator for each example was dissolved separately with a minimal amount of water to form a second liquid mixture. The first and second mixtures were combined to form liquid, curable obturation materials. The curable obturation materials polymerized to form hydrogel polymers.

Working time at room temperature, working time under vacuum, and/or setting times at 37° C. were observed, and reported in Table 5. After curing, percent shrinkage, percent swelling at 37° C., percent diametral swelling, percent leachability and/or percent water uptake were calculated as described herein and reported in Table 5. Solid, hard hydrogels were formed for Examples 5 through 13. Example 14 comprising diacrylate monomer in the absence of triacrylate did not form hard hydrogels; the resulting hydrogel was soft.

TABLE 5

Chemical Curing Reaction Mixtures And Cured Hydrogels.

| | Ex. 5 grams (wt %) | Ex. 6 grams (wt %) | Ex. 7 grams (wt %) | Ex. 8 grams (wt %) | Ex. 9 grams (wt %) | Ex. 10 grams (wt %) | Ex. 11 grams (wt %) | Ex. 12 grams (wt %) | Ex. 13 grams (wt %) | Ex. 14 grams (wt %) |
|---|---|---|---|---|---|---|---|---|---|---|
| water | 3.745 (24.32) | 3.752 (25.01) | 17.521 (34.97) | 2.249 (14.99) | 2.524 (24.99) | 2.522 (25.02) | 2.507 (24.97) | 2.630 (26.17) | 2.510 (24.90) | 2.630 (26.17) |
| potassium persulfate | 0.250 (1.62) | 0.081 (0.54) | 0.130 (0.26) | 0.080 (0.53) | 0.029 (0.29) | 0.043 (0.43) | 0.030 (0.30) | 0.030 (0.30) | 0.030 (0.30) | 0.030 (0.30) |
| triethanol-amine | 0.090 (0.58) | 0.052 (0.35) | 0.140 (0.28) | 0.085 (0.57) | 0.030 (0.30) | 0.030 (0.30) | 0.040 (0.40) | 0.030 (0.30) | 0.035 (0.35) | 0.035 (0.35) |
| ethoxy-lated trimethylol-propane triacrylate | 6.919 (44.93) | 7.189 (47.93) | 19.050 (38.02) | 8.649 (57.66) | 4.960 (49.11) | 4.83 (47.92) | | 4.795 (47.71) | 2.481 (24.61) | |
| poly(ethylene glycol) diacrylate | 0.189 (1.23) | 0.195 (1.30) | 0.630 (1.26) | 0.189 (1.26) | | 0.135 (1.34) | 4.952 (49.32) | | 2.465 (24.45) | 4.815 (47.91) |
| methacrylic acid | 0.039 (0.25) | 0.034 (0.23) | 0.150 (0.30) | | | | | 0.023 (0.23) | 0.025 (0.25) | 0.024 (0.24) |
| methyacryloylocy-ethyl-succinate | | | | 0.036 (0.24) | | | | | | |
| [2-(acryloyloxy) ethyl] trimethyl-ammonium chloride | 0.378 (2.45) | | | | | | | | | |
| zinc oxide | 0.758 (4.92) | 0.749 (4.99) | 2.513 (5.02) | 0.752 (5.01) | 0.527 (5.22) | 0.509 (5.05) | 0.510 (5.08) | 0.516 (5.13) | 0.519 (5.15) | 0.502 (5.00) |
| barium sulfate | 3.019 (19.60) | 3.002 (20.01) | 10.035 (20.03) | 3.010 (20.07) | 2.030 (20.10) | 2.008 (19.92) | 2.001 (19.93) | 2.028 (20.18) | 2.013 (19.97) | 2.012 (20.02) |
| TOTAL | 15.39 (100) | 15.05 (100) | 50.17 (100) | 15.05 (100) | 10.10 (100) | 10.08 (100) | 10.04 (100) | 10.05 (100) | 10.08 (100) | 10.05 (100) |
| work time | 4 min | 6 min | 17 min | | | | | | | |
| set time | | <5 min | 12 min | | 5 min | 15 min | 15 min | | | |
| work time under vacuum | | 2 min | 4 min | | | | | | | |
| % shrinkage | | 2.92 | 7.5 | 3.8 | 5.6 | 1.26 | 2.86 | 0.87 | 2.01 | −3.27 |
| radiopacity | | 1.87 | 1.99 | 1.99 | | | | | | |
| % swelling at 37° C. | | | | | 28.9 | 28.13 | 40.27 | 31.24 | 35.64 | 41.58 |
| % diametral swelling | | | | | −2.01 | −1.86 | 12.8 | 3.91 | 6.92 | 12.19 |
| % leachable | | | | | 4.1 | 0.62 | −0.55 | 0.31 | 0.65 | 1.22 |
| % water uptake | | | | | | 1.7 | 15.1 | 6.15 | 10 | 16.4 |
| forms solid hydrogel | yes | yes | yes | yes | yes | yes | yes | yes | yes | no |

Examples 16-19

Two-part chemical curing (self-curing) reaction mixtures were prepared comprising aqueous diacrylate monomer solutions and radiopaque component. Curable reaction mixtures were made according to Table 6, wherein for each solution of Examples 16 through 19, all ingredients were combined except the initiators and stirred at ambient temperature to form a first mixture. Initiators were dissolved separately with a minimal amount of water to form a second liquid component. The first and second mixtures were liquids, which combined to form a liquid curable obturation material. The amount of each component is provided in Table 6, and the diacrylate was poly(ethylene glycol) diacrylate (PEG, Mn 700). The radiopaque agent for Examples 16 through 18 was barium chloride, and for Example 8, and diatrizoate sodium hydrate for Example 19.

Working time at room temperature, working0 time under vacuum, and setting times at 37° C. were calculated as provided herein and reported in Table 6. After curing, percent shrinkage, percent swelling at 37° C., percent diametral swelling, percent leachability and/or percent water uptake were determined and reported in Table 6. Solid, hard hydrogels were formed for Examples 17 through 19. Example 16, prepared without MBAA, resulted in a soft hydrogel. Radiopacity measurements taken for Examples 16 and 19, were greater than 2, at 2.22 and 2.9, respectively.

TABLE 6

Two-Part Chemical Curable Reaction Mixtures And Cured Hydrogels.

| | Ex. 16 grams (wt %) | Ex. 17 grams (wt %) | Ex. 18 grams (wt %) | Ex. 19 grams (wt %) |
|---|---|---|---|---|
| water | 14.130 (56.43) | 14.130 (56.43) | 14.130 (56.43) | 13.380 (53.43) |
| potassium persulfate | 0.060 (0.24) | 0.060 (0.24) | 0.060 (0.24) | 0.060 (0.24) |
| triethanolamine | 0.067 (0.27) | 0.069 (0.28) | 0.054 (0.22) | 0.064 (0.26) |
| poly(ethylene glycol) diacrylate | 5.639 (22.52) | 4.745 (18.95) | 4.882 (19.50) | 5.004 (19.98) |
| N,N'-methylenebis (acrylamide) (MBAA) | | 0.253 (1.01) | 0.139 (0.56) | 0.265 (1.06) |
| [2-(acryloyloxy) ethyl]trimethyl-ammonium chloride | 0.145 (0.58) | 0.765 (3.06) | 0.753 (3.01) | |
| barium chloride | 5.000 (19.97) | 5.014 (20.02) | 5.017 (20.04) | |
| diatrizoate sodium hydrate | | | | 6.269 (25.04) |
| TOTAL | 25.04 (100) | 25.04 (100) | 25.04 (100) | 25.04 (100) |
| work time | 10 min | 7 min | 14 min | 6.5 min |
| set time | 7 min | 4.5 min | 8 min | 5 min |
| work time under vacuum | 10 min | 5.5 min | 8 min | 3.5 min |
| % shrinkage | 5.84 | 1.75 | 2.31 | 7.9 |
| radiopacity | 2.22 | | | 2.9 |
| % swelling at 37° C. | 69.61 | 71.71 | 74.53 | |
| % diametral swelling | −2.42 | 3.2 | 8.26 | |

Example 20

A self-curing aqueous acrylate-based monomer solution was prepared that further comprised an antimicrobial agent, [2-(acryloyloxy)ethyl]trimethyl-ammonium chloride. The composition was prepared substantially according to Examples 5 through 19. All of components listed in Table 7 for Ex. 20 was combined and stirred at ambient temperature to form a first liquid mixture, except the initiator. The initiator was dissolved separately with a minimal amount of water to form a second liquid mixture. The first and second liquid mixtures were then combined to form the curable obturation material.

TABLE 7

Aqueous Diacrylate-Based Monomer Solution.

| Ingredients | Weight % |
|---|---|
| water | 52.5 |
| Radical Source/Initiators | |
| potassium persulfate | 0.25 |
| triethanolamine | 0.25 |
| Diacrylate | |
| poly(ethylene glycol) diacrylate-Mn 700 (PEG) | 20 |
| triethylene glycol dimethacrylate (TEGDMA) | 1 |
| Antimicrobial/Antibacterial reagents | |
| [2-(acryloyloxy)ethyl] trimethyl-ammonium Chloride (EGAA-QCl) | 1 |
| Radiopaque Agents | |
| diatrizoate sodium hydrate | 25 |

Examples 21-30

Light curing, heat curing and dual light and heat curing aqueous diacrylate solutions were prepared, and then cured to form hydrogel obturation materials. Components of the compositions are provided in Table 8.

TABLE 8

Aqueous Light, Heat and Dual Curable Materials.

| Components | Ex. 21 wt % | Ex. 22 wt % | Ex. 23 wt % | Ex. 24 wt % | Ex. 25 wt % | Ex. 26 wt % | Ex. 27 wt % | Ex. 28 wt % | Ex. 29 wt % | Ex. 30 wt % |
|---|---|---|---|---|---|---|---|---|---|---|
| water | 47.5 | 46.5 | 46.9 | 47.4 | 46.4 | 47.05 | 47.55 | 56.42 (14.138 g) | 70.52 (14.14 g) | 17.7 |
| 2,2-azobis[2-(2-imidazolin-2-yl) propane] dihydro-chloride (AIPH/VA-044) | | | | | 0.3 | 0.3 | 0.3 | 0.24 | 0.31 (0.06 g) | 0.3 |
| 2,2'-azobis[2-methyl-N-(2-hydroxyethyl)-propionamide (AMPH/VA-086) | 1.5 | 2.5 | 1.5 | 1 | 1.5 | 1 | 0.5 | | | |
| ethoxylated trimethylolpropane triacrylate (ETT) | | | | | | | | | | 40 |
| poly(ethylene glycol) diacrylate (PEG) (Mn 700) | 20 | 20 | 20 | 20 | 20 | 20 | 20 | 20.2 (5.063 g) | 24.04 (4.820 g) | 12 |

TABLE 8-continued

Aqueous Light, Heat and Dual Curable Materials.

| Components | Ex. 21 wt % | Ex. 22 wt % | Ex. 23 wt % | Ex. 24 wt % | Ex. 25 wt % | Ex. 26 wt % | Ex. 27 wt % | Ex. 28 wt % | Ex. 29 wt % | Ex. 30 wt % |
|---|---|---|---|---|---|---|---|---|---|---|
| N,N'-methylenebis (acrylamide) (MBAA) | 1 | 1 | 1 | 1 | 1 | 1 | 1 | | 1.28 (0.257 g) | |
| [2-(acryloyloxy)-ethyl] trimethyl-ammonium chloride (EGAA-QC1) | | | 0.5 | 0.5 | 0.5 | 0.5 | 0.5 | 3.02 (0.758 g) | 3.82 (0.765 g) | |
| barium chloride | | | | | | | | 20.13 (5.044 g) | | 30 |
| diatrizoate sodium hydrate | 30 | 30 | 30 | 30 | 30 | 30 | 30 | | | |
| sodium hydroxide | Added[1] | Added[1] | 0.15 | 0.15 | 0.3 | 0.15 | 0.15 | | | |
| Total: | 100.0 | 100.0 | 100.0 | 100.0 | 100.0 | 100.0 | 100.0 | 100.0 (25.1 g) | 100.0 (20.1 g) | 100.0 |
| work time @ RT-non-degassed-dental light | 20 s-hard | 10 s-hard | 20 s-not hard | 20 s-not hard | 20 s-set | 30 s-set | 30 s-set | | | |
| work time under vacuum; degassed-dental light | | | 5 s-hard | 5 s-hard | 5 s-set | 5 s-hard | 5 s-hard | | | 45 min. at 37° C.-set |
| formed solid hydrogel | yes | yes | yes | yes | yes | yes | yes | no | no | yes |

[1]Sodium hydroxide-added until homogenous solution was achieved

Compositions of Exs. 21 through 24 were polymerizable upon exposure to light energy (i.e., dental light). Compositions of Exs. 25 through 27 were dual-curable (by sequential exposure to light and heat energy at physiological temperatures). Exs. 28 through 30 were prepared as heat-curable only polymerizable mixtures.

Ex. 24 (light cure initiator only) and Ex. 27 (light and heat cure initiators) were light cured in clear and black tubes by exposure to a dental light, and the cure depth was measured for non-degassed and degassed samples. The measured cure depth for samples prepared according to Ex. 24 cured for 10 seconds was 3.50 mm for the non-degassed sample in the clear tube and 8.30 mm in black tube, and 17.75 mm for the degassed sample in a clear tube and 10.75 mm for a degassed sample in a black tube. The measured cure depth for non-degassed samples prepared according to Ex. 27, cured for 30 seconds in a black tube, was 10 mm, and when cured for 40 seconds in a clear tube, was 8.5 mm; a degassed sample cured for 5 seconds in a clear tube had a cure depth of 20 mm, and a sample cured for 10 seconds had a cure depth of 10.5 mm in black tube. Example 27 had a radiopacity of 3.65 and a hardness (Shore OO) of 35, and a viscosity of 14.18 cP at 21.6° C. (measured on a Brookfield viscometer).

The heat curable-only mixture of Ex. 30, had a triacrylate to diacrylate wt % ratio of about 40:12, and about 30 wt % of barium chloride, and a Shore OO hardness value of 91 (degassed, 37° C. oven) and a Shore A hardness value of 73 (degassed, 37° C.). Exs. 28 and 29 having only heat curing initiators, and diacrylate with no triacrylate, cured to a soft gel and did not form a hard, solid hydrogel.

Examples 31-36

Curable hydrogel obturation materials were prepared from light curing acrylate (triacrylate/diacrylate) compositions with PPD initiator and multiple co-initiators. Samples were prepared comprising multiple light cure initiators and co-initiators as provided in Table 9, and then cured upon exposure to a dental light.

TABLE 9

Triacrylate/Diacrylate Light Cured Hydrogel Materials.

| Components | Ex. 31 (wt %) | Ex. 32 (wt %) | Ex. 33 (wt %) | Ex. 34 (wt %) | Ex. 35 (wt %) | Ex. 36 (wt %) |
|---|---|---|---|---|---|---|
| water | 23.96 | 23.99 | 24.00 | 24.37 | 23.89 | 16.53 |
| 1-phenyl-1,2-propanedione (PPD) | 0.86 | 0.86 | 0.86 | 0.86 | 0.86 | 0.60 |
| N-phenylglycine | | 0.87 | | | | |
| 2-pyrrolidinone | | | | 0.49 | | |
| dimethylaminoethyl acrylate (DMAEA) | 0.90 | | | | | 0.63 |
| triethanolamine (TEOA) | | | 0.60 | | | |

TABLE 9-continued

Triacrylate/Diacrylate Light Cured Hydrogel Materials.

| Components | Ex. 31 (wt %) | Ex. 32 (wt %) | Ex. 33 (wt %) | Ex. 34 (wt %) | Ex. 35 (wt %) | Ex. 36 (wt %) |
|---|---|---|---|---|---|---|
| L-arginine | | | | | 0.68 | |
| ethoxylated trimethylolpropane triacrylate | 57.14 | 57.14 | 57.14 | 57.14 | 57.14 | 40.00 |
| poly(ethylene glycol) diacrylate (PEG, Mn 700) | 17.14 | 17.14 | 17.14 | 17.14 | 17.14 | 12.00 |
| diatrizoate sodium hydrate | | | | | | 30.00 |
| TOTAL | 100.00 | 100.00 | 100.00 | 100.00 | 100.00 | 100.00 |
| hardness | Shore A-degassed 68-10 s 74-20 s 74-40 s | Shore A-degassed 78.5-20 s | Shore A-degassed 54-20 s | Shore A-degassed 78-20 s | Shore A-0 degassed-20s Shore OO-32-degassed-20 s | Shore A-degassed 0-10 s 12-20 s 25-30 s 48-40 s |
| cure depth | degassed 5 mm-10 s 28 mm-20 s 28.5 mm-30 s 31 mm-40 s | degassed 19 mm-20 s | degassed 26 mm-20 s | degassed 15 mm-20 s | degassed 19 mm-20 s | degassed 1.5 mm-10 s 2.54 mm-20 s 4.03 mm-30 s 6 mm-40 s |
| forms solid hydrogel | Y | Y | Y | Y | Y | Y |

The examples comprised about 50 wt % to about 75 wt % of triacrylate:diacrylate mixture (in a ratio of approximately 3.3:1), and about 16 wt % to 25 wt % water. Hardness values for the cured materials measured on a Brookfield viscometer are reported in Table 9.

Examples 37-43

Acrylate compositions were prepared from triacrylate and diacrylate monomers, light curing initiators CQ or CCQ, and multiple co-initiators. Samples were prepared according to Table 10, and then exposed to a dental light.

TABLE 10

Acrylate Compositions With Light Cure Initiators.

| Components | Ex. 37 (wt %) | Ex. 38 (wt %) | Ex. 39 (wt %) | Ex. 40 (wt %) | Ex. 41 (wt %) | Ex. 42 (wt %) | Ex. 43 (wt %) |
|---|---|---|---|---|---|---|---|
| water | 23.57 | 23.61 | 22.1 | 24.45 | 24.11 | 19.5 | 17.2 |
| 2,2'-azobis[2-methyl N-(2-hydroxyethyl) propionamide (AMPH/VA-086) | 0.71 | | | | | 0.50 | 0.80 |
| camphorquinone (CQ) | | | | 0.62 | 0.86 | | |
| 7,7-dimethyl-2,3-dioxobicyclo[2.2.1] heptane-1-carboxylic acid (CCQ) | | 0.86 | 0.86 | | | | |
| dimethylaminoethyl acrylate (DMAEA) | | 1.24 | | | 0.74 | | |
| 1-vinyl-2-pyrrolidone | | | 1.33 | 0.87 | | | |
| ethoxylated trimethylolpropane triacrylate | 57.14 | 57.14 | 57.14 | 57.16 | 57.14 | 40.00 | 40.00 |
| poly(ethylene glycol) diacrylate (PEG, Mn 700) | 17.14 | 17.14 | 17.14 | 16.91 | 17.14 | 10.00 | 12.00 |

TABLE 10-continued

Acrylate Compositions With Light Cure Initiators.

| Components | Ex. 37 (wt %) | Ex. 38 (wt %) | Ex. 39 (wt %) | Ex. 40 (wt %) | Ex. 41 (wt %) | Ex. 42 (wt %) | Ex. 43 (wt %) |
|---|---|---|---|---|---|---|---|
| N,N'-methylenebis (acrylamide) (MBAA) | 1.43 | | 1.43 | | | | |
| 5-acrylamido-2,4,6-triiodo isophdialic acid | | | | | | 30.00 | 30.00 |
| TOTAL | 100.00 | 100.00 | 100.00 | 100.00 | 100.00 | 100.00 | 100.00 |
| hardness | Shore A-degassed 62.5-10 s 76-15 s 82.5-20 s 85-40 s | Shore A-degassed 35-10 s 57-20 s 76- 40 s | Shore A-degassed 76-10 s 80-20 s 82-40 s | Shore A-degassed 18-10 s 30-20 s 52-30 s 72-40 s | Shore A-degassed 0-10 s 24-20 s 26.5-30 s 66-40 s | | Shore OO 93-degassed Shore A 52-degassed |
| cure depth | degassed 20 mm-10 s 21 mm-20 s 34 mm-30 s 41 mm-40 s | degassed 26 mm-10 s 27 mm-20 s 31 mm-30 s 31 mm-40 s | degassed 26 mm-20 s 31 mm-40 s | degassed 17 mm-10 s 22 mm-20 s 28 mm-30 s 32 mm-40 s | degassed 9.64 mm-10 s 14.97 mm-20 s 15.95 mm-30 s 11.5 mm-40 s | | 14 mm-degassed-40 s |
| forms solid hydrogel | Y | Y | Y | Y | Y | N | Y |

Examples 44-47

Hydrogel polymer obturation materials were prepared and tested for antimicrobial activity against *E. coli* and *E. faecalis*. Compositions for Examples 30 through 55 are provided in Table 11.

TABLE 11

Hydrogel Polymer Obturation Materials Comprising

| Components | Ex. 44 (wt %) | Ex. 45 (wt %) | Ex. 46 (wt %) | Ex. 47 (wt %) |
|---|---|---|---|---|
| water | 27.1 | 25.1 | 25.1 | 33.1 |
| potassium persulfate | 0.25 | 0.25 | 0.25 | 0.25 |
| triethanolamine | 0.25 | 0.25 | 0.25 | 0.25 |
| ethoxylated trimethylolpropane triacrylate | 48.00 | 48.00 | 45.00 | 45.00 |
| poly(ethylene glycol) diacrylate (PEG) (Mn 700) | 1.20 | 1.20 | 1.20 | 1.20 |
| methacrylic acid | 0.2 | 0.2 | 0.2 | 0.2 |
| [2-(Acryloyloxy)-ethyl] trimethyl-ammonium chloride | 3 | | 3 | |
| zinc oxide | | 5 | 5 | |
| barium sulfate | 20 | 20 | 20 | 20 |

Ex. 44 comprised 3 wt % [2-(acryloyloxy)ethyl] trimethyl-ammonium chloride, Ex. 45 comprised 5 wt % zinc oxide and Ex. 46 comprised both 3 wt % [2-(acryloyloxy) ethyl] trimethyl-ammonium chloride and 5 wt % zinc oxide. Ex. 47 had neither [2-(acryloyloxy)ethyl] trimethyl-ammonium chloride nor zinc oxide. *E. coli* CFU was reduced from $1 \times 10^6$ at Day 0 to <10 at Days 1, 14 and 28, for Exs. 44 and 46. *E. coli* CFU was reduced from $1 \times 10^6$ at Day 0 to <10 at Day 14 and Day 28 for Ex. 45 and Ex. 47. At Day 1, *E. coli* CFU was reduced from $1 \times 10^6$ to $2.3 \times 10^4$, and $7.0 \times 10^4$, for Ex. 45 and Ex. 47, respectively.

*E. faecalis* CFU reduction was from $1.1 \times 10^6$ to $1.5 \times 10^4$, $2.7 \times 10^4$, $2.2 \times 10^3$ and $2.6 \times 10^4$ at Day 1 for Exs. 44, 45, 46 and 47, respectively. For Exs. 44, 45, 46 and 47, *E. faecalis* CFU was <10 at Day 14 and Day 28. The samples were prepared and tested according to USP <51> Antimicrobial Effectiveness Testing.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products. For example, any of the components for an energy storage system described herein can be provided separately, or integrated together (e.g., packaged together, or attached together) to form an energy storage system.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount, depending on the desired function or desired result.

The headings contained in this document, if any, are for convenience only and do not necessarily affect the scope or meaning of the devices and methods disclosed herein.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of filling a tooth or root canal, comprising:
   identifying a tooth having a cavity or a root canal in need of filling;
   positioning a curable mixture within the cavity or root canal; and
   curing the curable mixture within the cavity or root canal;
   wherein the curable mixture comprises:
   (a) a water-soluble acrylate-based monomer, a water-soluble acrylamide-based monomer, a water-soluble chelating monomer, or a mixture thereof;
   (b) a free-radical polymerization initiator;
   (c) a radiopaque material; and
   (d) an aqueous carrier having a pH in the range of about 7.0 to about 8.4;
   wherein the ingredients (a), (b), (c), and (d) are selected to provide the curable mixture with properties suitable for use as a tooth filling after curing of the curable mixture to form a cured mixture by a polymerization of ingredient (a) that is initiated by ingredient (b).

2. The curable mixture of claim 1, wherein the free radical polymerization initiator is selected from the group consisting of a light initiator, a thermal initiator, and combinations thereof.

3. The curable mixture of claim 1, wherein the water-soluble acrylamide-based monomer is selected from the group consisting of 3-acrylamidopropyl trimethylammonium chloride, 3-methacrylamidopropyl trimethylammonium chloride, 3-acrylamidopropyl trimethylammonium methyl sulfate, 3-methacrylamidopropyl trimethylammonium methyl sulfate, combinations thereof.

4. The curable mixture of claim 1, wherein the water-soluble acrylate-based monomer is selected from the group consisting of [2-(methacryloyloxy)ethyl] trimethylammonium chloride, [2-(acryloyloxy)ethyl] trimethylammonium chloride, [2-(acryloyloxy)ethyl] trimethylammonium methyl sulfate, [2-(methacryloyloxy)ethyl] trimethylammonium methyl sulfate, (hydroxyethyl)methacrylate (HEMA), poly(ethylene glycol) diacrylate, ethoxylated trimethylolpropane triacrylate, and combinations thereof.

5. The curable mixture of claim 1, wherein the chelating monomer is selected from the group consisting of 4-methacryloxyethyl trimellitic acid (4-MET), glycerol phosphate dimethacrylate (GPDM), and combinations thereof.

6. The curable mixture of claim 1, wherein the radiopaque material is selected from the group consisting of a polymerizable radiopaque monomer, a radiopaque salt, and combinations thereof.

7. The curable mixture of claim 6, wherein the radiopaque material is selected from the group consisting of sodium diatrizoate hydrate, iodophenyl functionalized polyethylene glycol, a water soluble radiopaque aromatic acid derived (meth)acrylate, and combinations thereof.

8. The curable mixture of claim 7, wherein the water soluble radiopaque aromatic acid derived (meth)acrylate is 5-acrylamido-2,4,6 triiodo isophthalic acid.

9. The curable mixture of claim 1, further comprising a polymerization cross-linker.

10. The curable mixture of claim 9, wherein the polymerization cross-linker is selected from the group consisting of N,N'-methylenebis(acrylamide) (MBAA), triethylene glycol dimethacrylate (TEGDMA), and combinations thereof.

11. The curable mixture of claim 2, wherein the light initiator is selected from the group consisting of camphorquinone (CQ), 7,7-dimethyl-2,3-dioxobicyclo [2.2.1] heptane-1-carboxylic acid (CCQ), 1-phenyl-1,2-propanedione (PPD), 2,2'-azobis[2-methyl-N-(2-hydroxyethyl)propionamide (VA-086), and combinations thereof.

12. The curable mixture of claim 1, further comprising a co-initiator selected from the group consisting of N-phenylglycine, 2-pyrrolidinone, dimethylaminoethyl acrylate (DMAEA), triethanolamine (TEOA), 1-vinyl-2-pyrrolidone and L-arginine, and combinations thereof.

13. The curable mixture of claim 2, wherein the thermal initiator comprises 2,2'-azobis[2-(2-imidazolin-2-yl) propane] dihydrochloride.

14. The curable mixture of claim 1, wherein the free-radical polymerization initiator comprises potassium persulfate and triethanolamine.

15. The curable mixture of claim 1, further comprising methacrylic acid.

16. The curable mixture of claim 1, comprising from 20 wt % to 60 wt % of the aqueous carrier, based on the weight of the curable mixture.

17. A method of filling a root canal with a hydrogel polymer, comprising:
identifying a tooth having a root canal in need of filling;
positioning a curable mixture within a handpiece, comprising delivering the curable mixture to the handpiece in two liquid parts;
forming a liquid jet within the handpiece and using the liquid jet to deliver the two parts;
partially curing the curable mixture within the root canal with light energy; and
exposing the partially cured mixture within the root canal to heat to form a cured hydrogel polymer within the root canal;
wherein the curable mixture comprises:
(a) a water-soluble acrylate-based monomer, a water-soluble acrylamide-based monomer, a water-soluble chelating monomer, or a mixture thereof;
(b) a free-radical polymerization initiator;
(c) a radiopaque material; and
(d) an aqueous carrier having a pH in the range of about 7.0 to about 8.4;
wherein the ingredients (a), (b), (c), and (d) are selected to provide the curable mixture with properties suitable for use as a tooth filling after curing of the curable mixture to form a cured mixture by a polymerization of ingredient (a) that is initiated by ingredient (b).

18. A curable mixture of ingredients, comprising:
(a) 20 wt. % to 50 wt % poly(ethylene glycol) diacrylate (PEG);
(b) 0.5 wt % to 1.5 wt. % N,N'-methylenebis(acrylamide) (MBAA);
(c) 0.2 wt. % to 1.5 wt % potassium persulfate;
(d) 0.2 wt. % to 0.6 wt % triethanolamine;
(e) 5 wt % to 30 wt. % of 5-acrylamido-2,4,6-triiodo isophthtalic acid; and
(f) 20 wt % to 60 wt % of an aqueous carrier,
wherein the ingredients are selected to provide the curable mixture with properties suitable for use as a tooth filling after curing of the curable mixture to form a cured mixture.

19. A curable mixture of ingredients, comprising:
(a) 0.1 wt % to 0.5 wt % 2,2'-azobis[2-(2-imidazolin-2-yl) propane] dihydrochloride;
(b) 20 wt % to 50 wt % ethoxylated trimethylolpropane triacrylate;
(c) 10 wt % to 15 wt % poly(ethylene glycol) diacrylate (PEG);
(d) 5 wt % to 35 wt % 5-acrylamido-2,4,6-triiodo isophthalic acid; and
(f) 15 wt % to 50 wt % water.

20. A curable mixture of ingredients, comprising:
(a) 0.1 wt % to 0.5 wt % 2,2'-azobis[2-(2-imidazolin-2-yl) propane] dihydrochloride;
(b) 0.1 wt % to 2.5 wt % of a light cure initiator;
(c) 10 wt % to 30 wt % poly(ethylene glycol) diacrylate;
(d) 0.5 wt % to 2 wt % N,N'-methylenebis (acrylamide) (MBAA);
(e) optionally, 0.1 wt % to 1 wt % [2-(acryloyloxy)ethyl] trimethyl-ammonium chloride; and
(f) an aqueous carrier,
wherein the ingredients are selected to provide the curable mixture with properties suitable for use as a tooth filling after curing of the curable mixture to form a cured mixture.

21. A curable mixture of ingredients, comprising:
(a) 20 wt % to 50 wt % ethoxylated trimethylolpropane triacrylate;
(b) 10 wt % to 15 wt % poly(ethylene glycol) diacrylate;
(c) 0.1 wt % to 3 wt % 2,2'-azobis[2-methyl-N-(2-hydroxyethyl)propionamide;
(d) 5-acrylamido-2,4,6-triiodo isophthalic acid; and
(e) 15 wt % to 55 wt % aqueous carrier;
wherein the ingredients are selected to provide the curable mixture with properties suitable for use as a tooth filling after curing of the curable mixture to form a cured mixture.

22. A method of filling a tooth or root canal, comprising:
identifying a tooth having a cavity or a root canal in need of filling;
positioning the curable mixture of claim 18 within the cavity or root canal; and
curing the curable mixture within the cavity or root canal.

23. A method of filling a tooth or root canal, comprising:
identifying a tooth having a cavity or a root canal in need of filling;
positioning the curable mixture of claim 19 within the cavity or root canal; and
curing the curable mixture within the cavity or root canal.

24. A method of filling a tooth or root canal, comprising:
identifying a tooth having a cavity or a root canal in need of filling;
positioning the curable mixture of claim 20 within the cavity or root canal; and
curing the curable mixture within the cavity or root canal.

25. A method of filling a tooth or root canal, comprising:
identifying a tooth having a cavity or a root canal in need of filling;
positioning the curable mixture of claim 21 within the cavity or root canal; and
curing the curable mixture within the cavity or root canal.

* * * * *

UNITED STATES PATENT AND TRADEMARK OFFICE
CERTIFICATE OF CORRECTION

PATENT NO. : 11,680,141 B2
APPLICATION NO. : 16/865208
DATED : June 20, 2023
INVENTOR(S) : Zaza Gomurashvili et al.

It is certified that error appears in the above-identified patent and that said Letters Patent is hereby corrected as shown below:

In the Specification

In Column 3, Line 52, delete "(° 25 C.)" and insert --(25° C.)--.

In Column 12, Line 10, delete "acrylamidolpropyl)" and insert --acrylamidopropyl)--.

In Column 12, Line 18, delete "Eschericia" and insert --Escherichia--.

In Column 22, Line 12 (Approx.), delete "#54506" and insert --#S4506--.

In Columns 23-24, Line 23, TABLE 5, delete "methyacryloylocy-" and insert --methacryloyloxy- --.

In Columns 23-24, Line 50, TABLE 5, delete "eachable" and insert --leachable--.

In Column 24, Line 57, delete "working0" and insert --working--.

In Columns 27-28, Line 8, TABLE 8-continued, delete "QC1)" and insert --QCl)--.

In Columns 29-30, Line 6, TABLE 9-continued, delete "trirnethylolpropane" and insert --trimethylolpropane--.

In Columns 31-32, Line 7, TABLE 10-continued, delete "isophdialic" and insert --isophthalic--.

In the Claims

In Column 35, Claim 11, Lines 10-11, delete "2,2'-azobis[2-methyl-N-(2-hydroxyethyl)propionamide" and insert --2,2'-azobis[2-methyl-N-(2-hydroxyethyl)propionamide]--.

In Column 35, Claim 18, Line 63, delete "isophthtalic" and insert --isophthalic--.

Signed and Sealed this
Twenty-second Day of August, 2023

Katherine Kelly Vidal
*Director of the United States Patent and Trademark Office*

CERTIFICATE OF CORRECTION (continued)
U.S. Pat. No. 11,680,141 B2

In Column 36, Claim 19, Line 14 (Approx.), delete "(f)" and insert --(e)--.

In Column 36, Claim 21, Lines 32-33, delete "2,2'-azobis[2-methyl-N-(2-hydroxyethyl)propionamide" and insert --2,2'-azobis[2-methyl-N-(2-hydroxyethyl)propionamide]--.